(12) United States Patent
Urano et al.

(10) Patent No.: US 12,221,649 B2
(45) Date of Patent: Feb. 11, 2025

(54) FLUORESCENT PROBE FOR DETECTING CARBOXYPEPTIDASE ACTIVITY

(71) Applicant: The University of Tokyo, Tokyo (JP)

(72) Inventors: Yasuteru Urano, Tokyo (JP); Mako Kamiya, Tokyo (JP); Yugo Kuriki, Tokyo (JP)

(73) Assignee: The University of Tokyo, Tokyo (JP)

( * ) Notice: Subject to any disclaimer, the term of this patent is extended or adjusted under 35 U.S.C. 154(b) by 764 days.

(21) Appl. No.: 17/298,477

(22) PCT Filed: Dec. 2, 2019

(86) PCT No.: PCT/JP2019/047000
§ 371 (c)(1),
(2) Date: May 28, 2021

(87) PCT Pub. No.: WO2020/111279
PCT Pub. Date: Jun. 4, 2020

(65) Prior Publication Data
US 2022/0017940 A1  Jan. 20, 2022

(30) Foreign Application Priority Data
Nov. 30, 2018 (JP) .................. 2018-225735

(51) Int. Cl.
*C12Q 1/37* (2006.01)
*C07F 9/655* (2006.01)
(Continued)

(52) U.S. Cl.
CPC ............... *C12Q 1/37* (2013.01); *C09K 11/06* (2013.01); *G01N 21/6428* (2013.01);
(Continued)

(58) Field of Classification Search
None
See application file for complete search history.

(56) References Cited

U.S. PATENT DOCUMENTS

2014/0057866 A1* 2/2014 McGuigan ............. A61K 45/06
514/51

FOREIGN PATENT DOCUMENTS

JP  2014-506913 A  3/2014
JP  2018-145126 A  9/2018
(Continued)

OTHER PUBLICATIONS

Machine generated English language translation of Urano (JP2018145126A, published on Sep. 20, 2018, of record in the IDS filed on May 28, 2021), obtained Mar. 28, 2024 (Year: 2024).*
(Continued)

*Primary Examiner* — Amy C Bonaparte
(74) *Attorney, Agent, or Firm* — Knobbe, Martens, Olson & Bear, LLP

(57) ABSTRACT

A compound is represented by the following general formula (I):

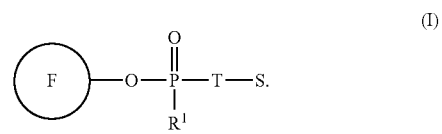

The compound or a salt thereof provides a fluorescent probe for detecting carboxypeptidase activity In the formula, $R^1$ represents an alkyl group having 1 to 6 carbon atoms or an alkoxy group having 1 to 6 carbon atoms; T represents an amino acid residue or a residue of an amino acid derivative; S represents a C-terminal amino acid residue.
(Continued)

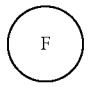

represents a fluorophore, and the fluorophore is a fluorophore in which an absorption/fluorescence wavelength greatly changes or a quenched state changes to a fluorescent state by elimination of the —P(=O)(—R$^1$)-T-S moiety.

5 Claims, 11 Drawing Sheets

(51) Int. Cl.
 C07F 9/6561 (2006.01)
 C09K 11/06 (2006.01)
 G01N 21/64 (2006.01)
 G01N 33/542 (2006.01)
(52) U.S. Cl.
 CPC ............ *G01N 33/542* (2013.01); *C07F 9/655* (2013.01); *C07F 9/6561* (2013.01); *G01N 2021/6439* (2013.01); *G01N 2333/948* (2013.01)

(56) References Cited

FOREIGN PATENT DOCUMENTS

WO WO 2001/064664 A1 9/2001
WO WO 2010/095450 A1 8/2010

OTHER PUBLICATIONS

Derudas ("The Application of Phosphoramidate Protide Technology to Acyclovir Confers Anti-HIV Inhibition" J. Med. Chem. 2009, 52, p. 5520-5530) (Year: 2009).*
Kuriki et al., "Establishment of molecular design strategy to obtain activatable fluorescent probes for carboxypeptidases." Journal of the American Chemical Society, Jan. 25, 2018, vol. 140, pp. 1767-1773.
International Search Report in International Application No. PCT/JP2019/047000, mailed on Feb. 25, 2020.

* cited by examiner

[FIG. 1]
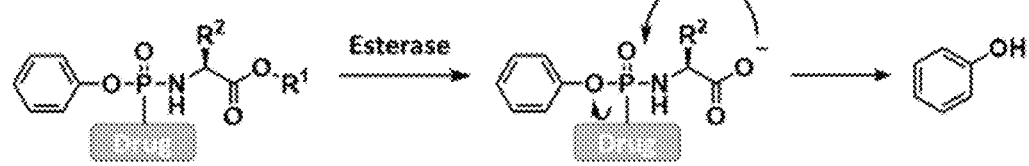
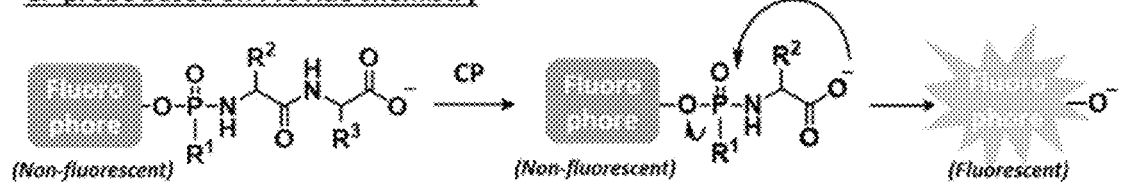

[FIG. 2]
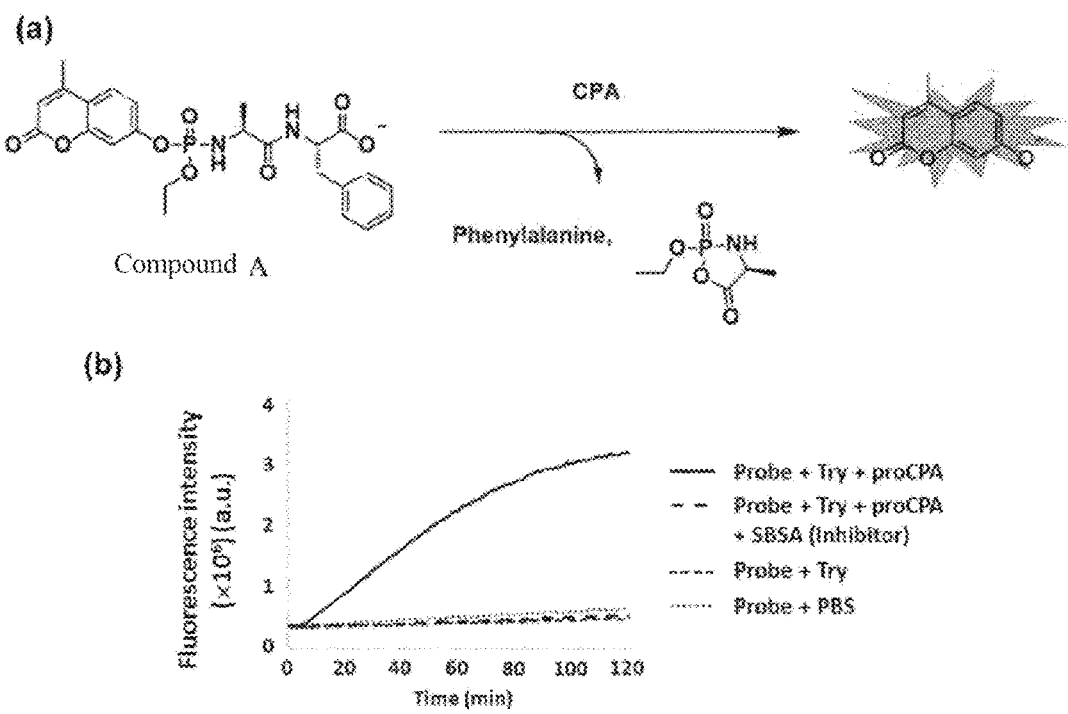
(a) Reaction scheme of Compound A with CPA. (b) 10 μM Compound A in PBS(-) was incubated with 5 ng CPA activated by 1.5 μg trypsin in the presence or absence of 100 μM inhibitor ((S)-benzylsuccinic acid) containing 0.1 % DMSO as a co-solvent. Incubated at 37 °C. Ex / Em = 355 / 460 nm. n=4. Abbreviations: Try; trypsin, SBSA; (S)-benzylsuccinic acid.

[FIG. 3]
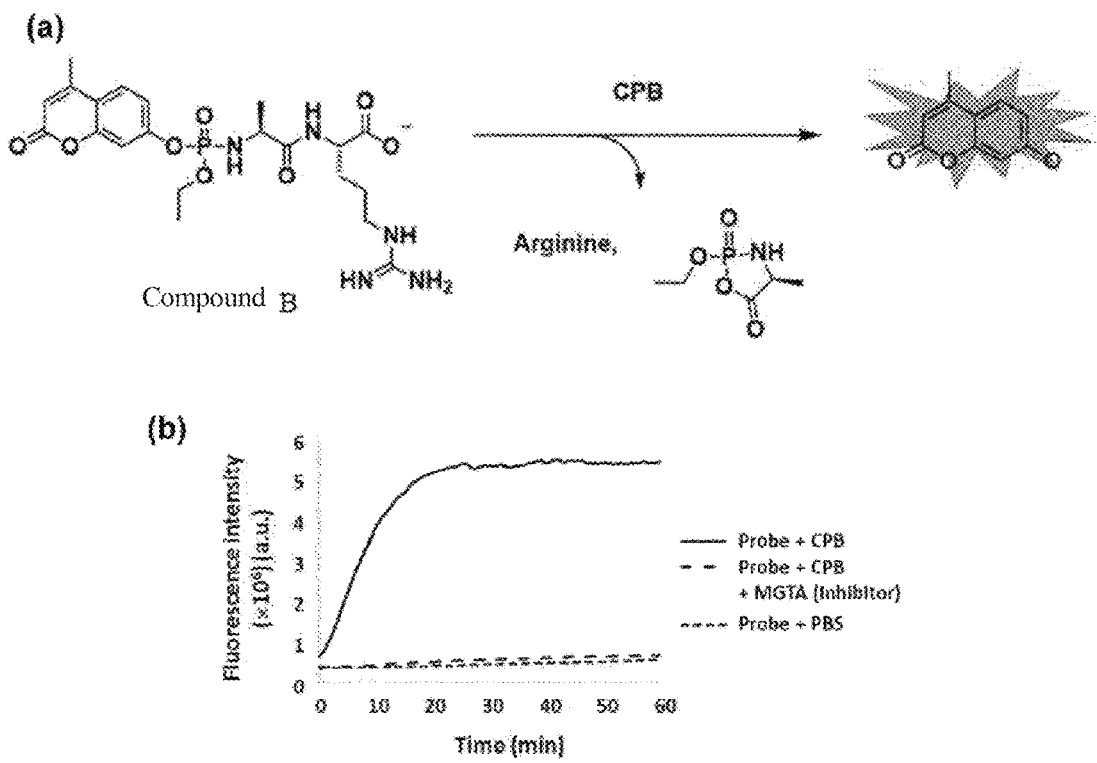
(a) Reaction scheme of Compound B with CPB. (b) 10 μM Compound B in PBS(-) was incubated with 5 ng CPB in the presence or absence of 100 μM inhibitor (MGTA) containing 0.1 % DMSO as a co-solvent. Incubated at 37 °C. Ex / Em = 355 / 460 nm. n=4.

[FIG. 4]
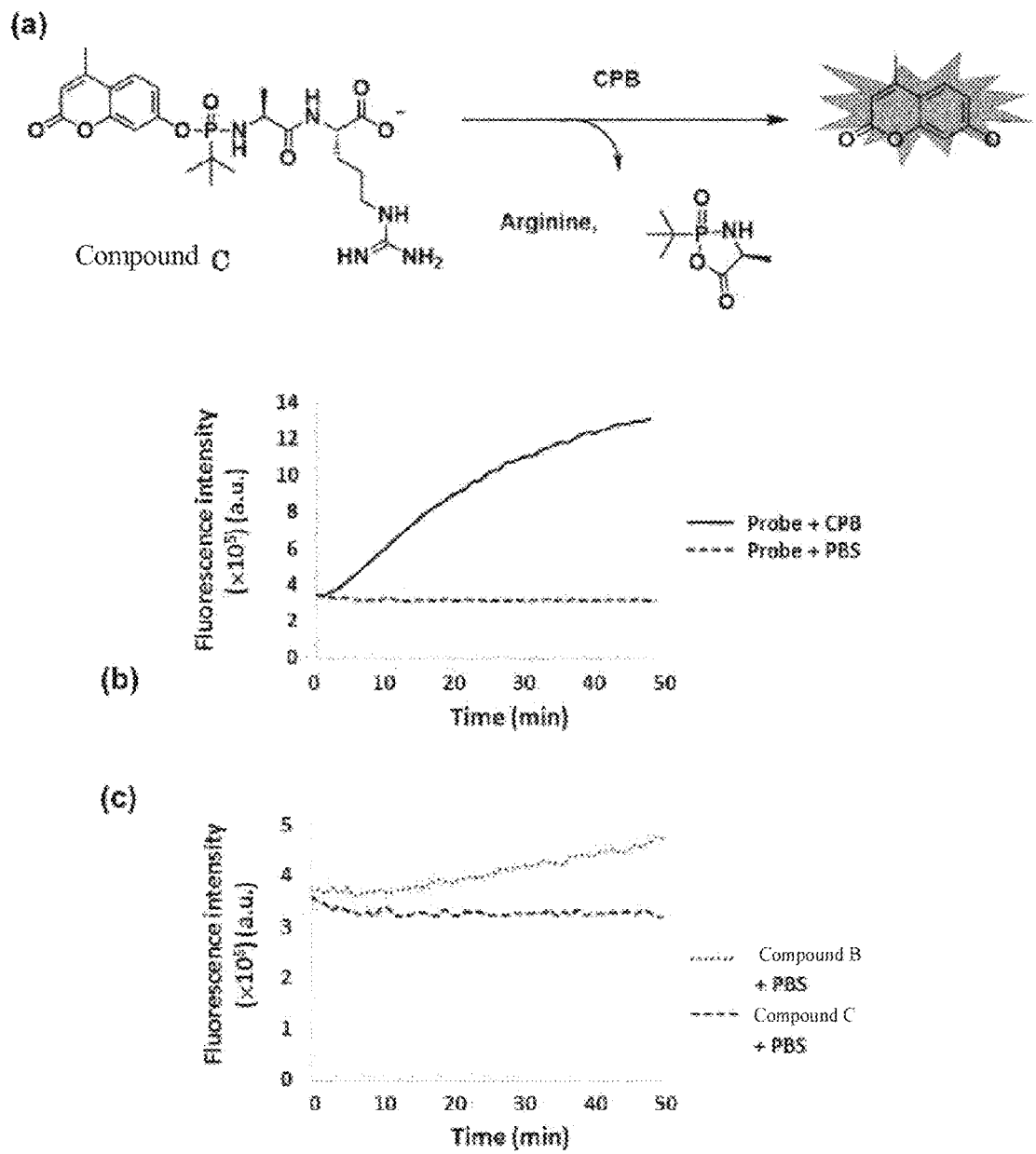
(a) Reaction scheme of Compound C with CPB. (b) 10 μM Compound C in PBS(-) was incubated in the presence or absence 5 ng CPB containing 0.1 % DMSO as a co-solvent. Incubated at 37 °C. Ex / Em = 355 / 460 nm. n=4. (c) Comparison of stability of Compound B and Compound C. 10 μM Compound B or Compound C in PBS(-) was incubated in the absence of CPB at 37 °C. Ex / Em = 355 / 460 nm. n=4.

[FIG. 5]
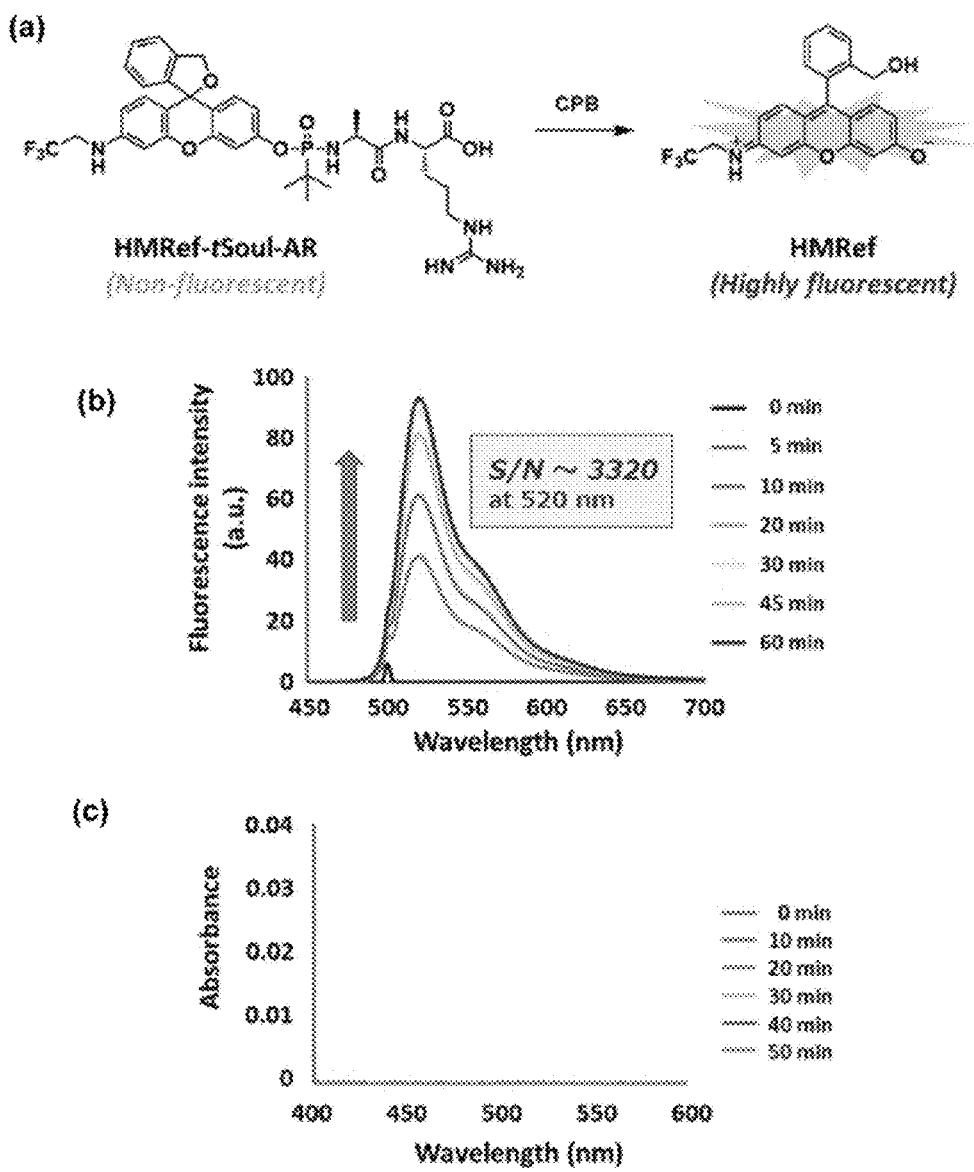
(a) Reaction scheme of HMRef-tSoul-AR with CPB. (b) Fluorescence increase of 1 μM HMRef-tSoul-AR in PBS(-) incubated with 30 μg CPB containing 0.1 % DMSO as a co-solvent. Incubated at 25 °C. Excitation wavelength was 498 nm. (c) Absorption change of 1 μM HMRef-tSoul-AR in PBS(-) over 50 min at 25 °C.

[FIG. 6]
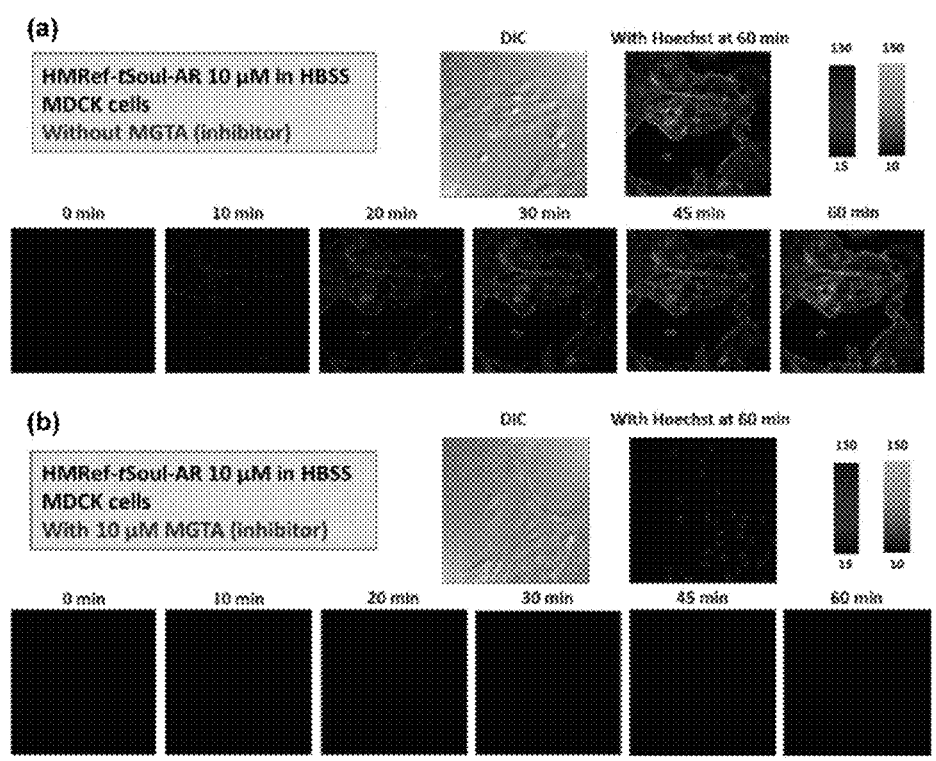
(a), (b) Fluorescent images of MDCK cells with 10 μM HMRef-tSoul-AR in HBSS in the (a) absence or (b) presence of 10 μM MGTA. Ex / Em = 488 / 500-550 nm. Laser power 5%, PMT 600 V. 10 μM Hoechst 33342 was co-incubated. For imaging of Hoechst signal, Ex / Em = 405 / 430-460 nm. Laser power 3%, PMT 1000 V, SP8.

[FIG. 7]

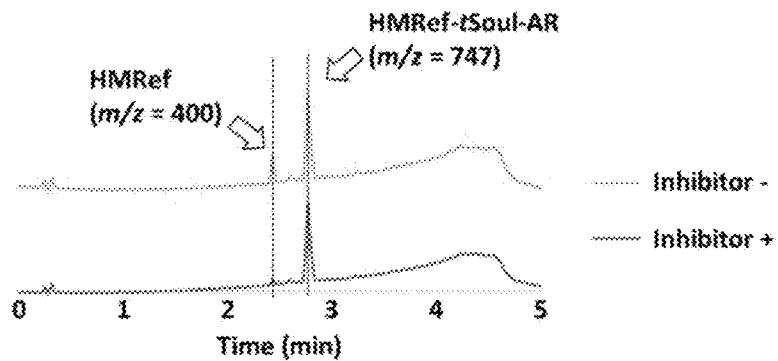

UPLC analysis of culture medium of MDCK cells incubated with 20 μM HMRef-tSoul-AR in the presence or absence of 10 μM MGTA.

MDCK cells were incubated with 20 μM HMRef-tSoul-AR in HBSS in the presence or absence of 10 μM MGTA at 37 °C for 20 hours. Elution was done with a linear gradient of C/D = 95/5 to 5/95 in 4 min. Detected at 254 nm.

[FIG. 8]

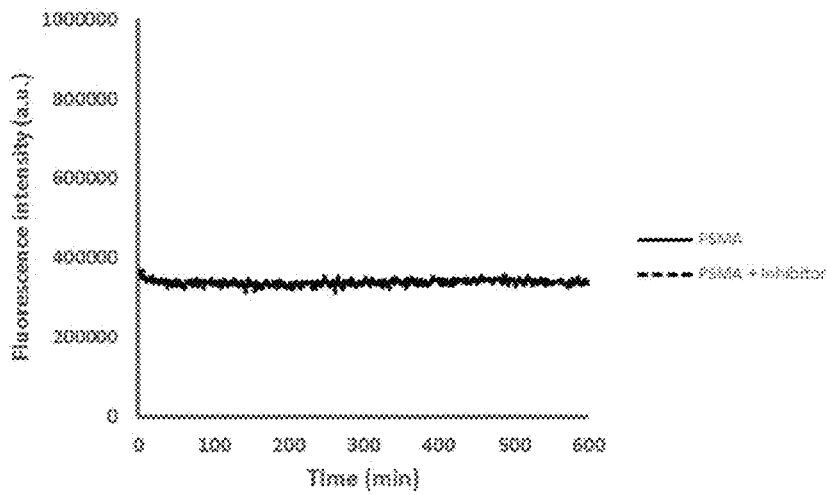

10 μM 4MU-tSoul-AE in TBS buffer was incubated with 22 ng PSMA in the presence or absence of 10 μM inhibitor (2-PMPA) containing 0.1 % DMSO as a co-solvent. Incubated at 37 °C. Ex / Em = 355 / 460 nm. n=3.

[FIG. 9]
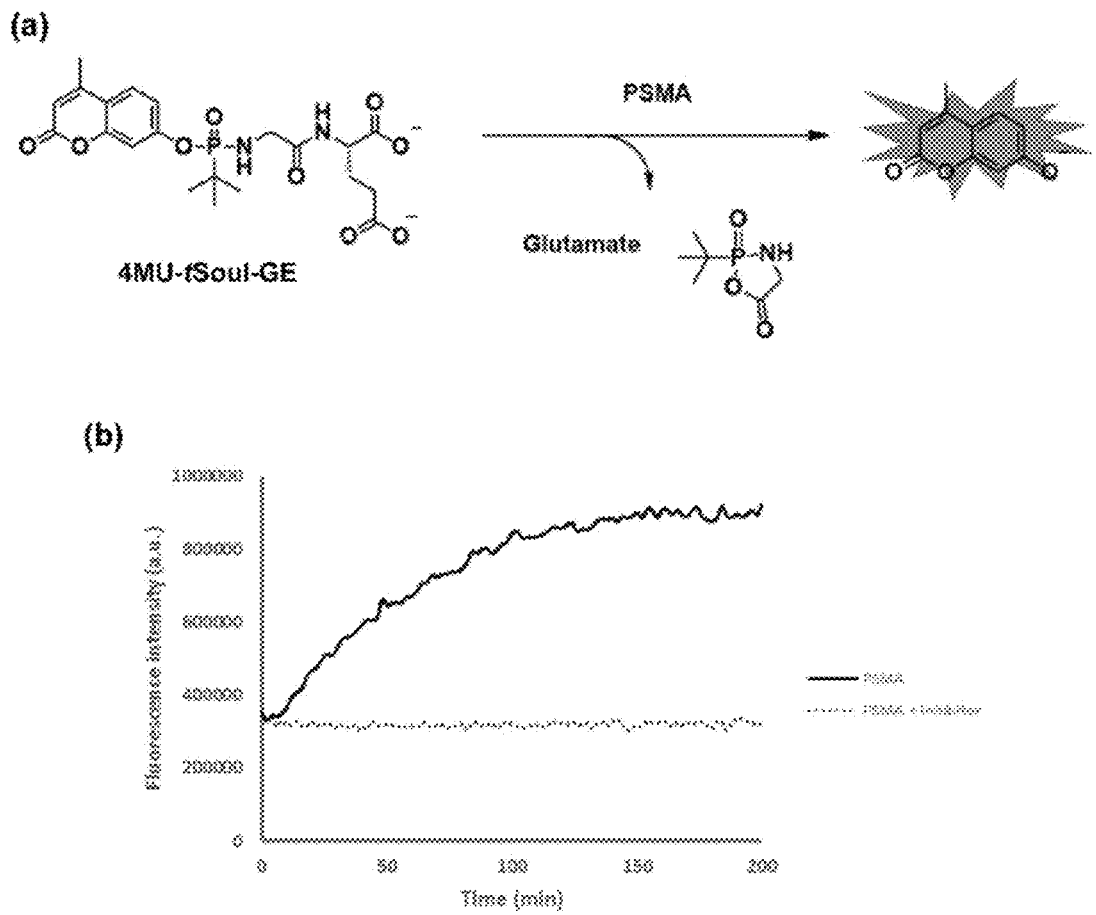
(a) Reaction scheme of 4MU-fSoul-GE with PSMA. (b) 10 μM 4MU-fSoul-GE in TBS buffer was incubated with 22 ng PSMA in the presence or absence of 10 μM inhibitor (2-PMPA) containing 0.1 % DMSO as a co-solvent. Incubated at 37 °C. Ex / Em = 355 / 460 nm. n=3.

[FIG. 10]
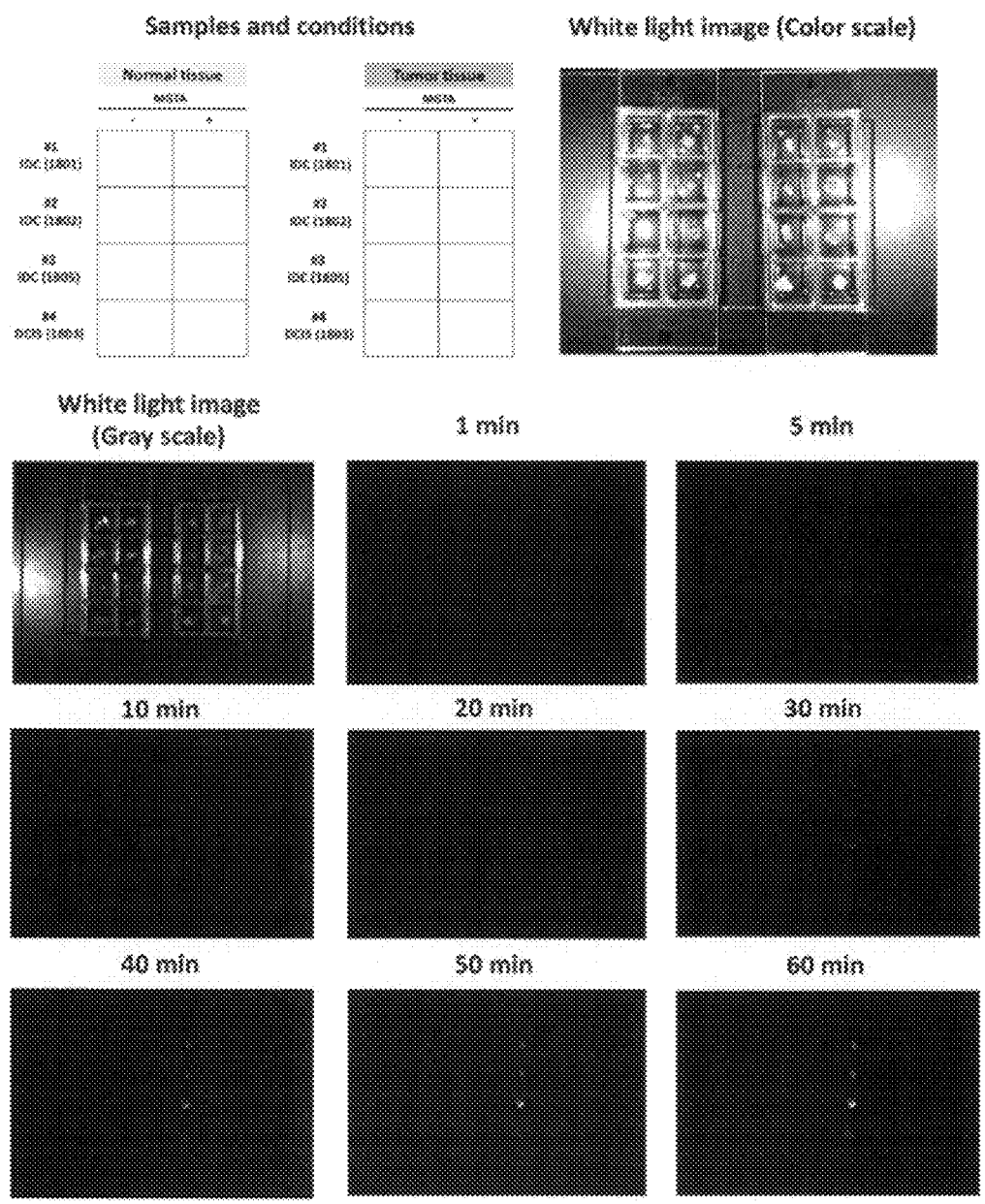

[FIG. 11]
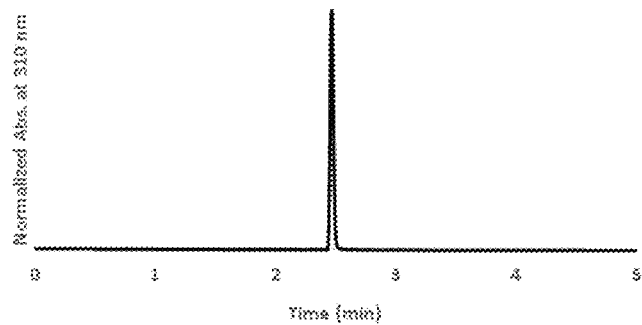
[FIG. 12]
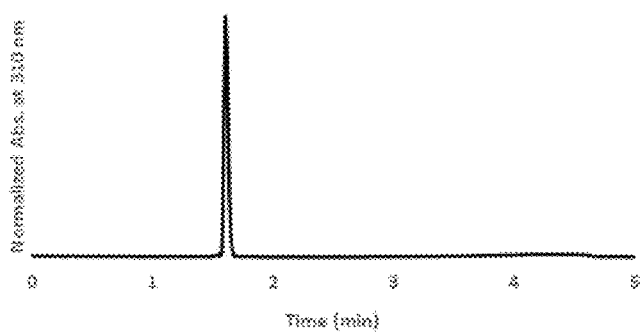
[FIG. 13]
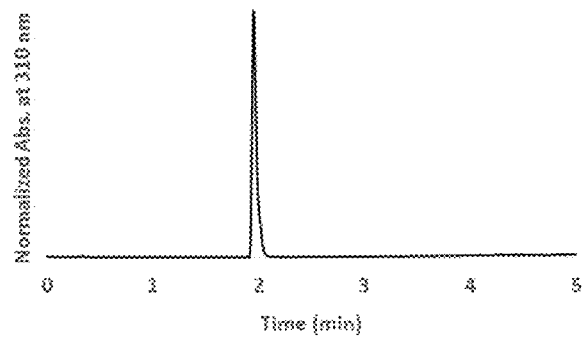

[FIG. 14]
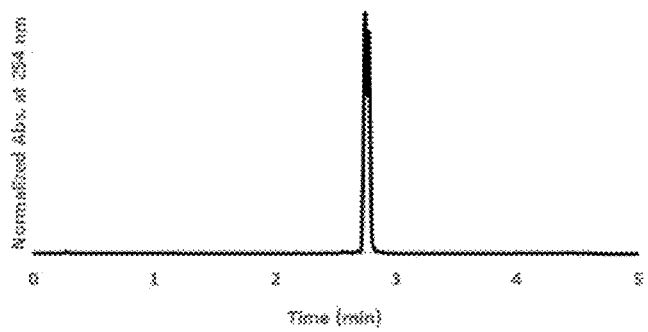
[FIG. 15]
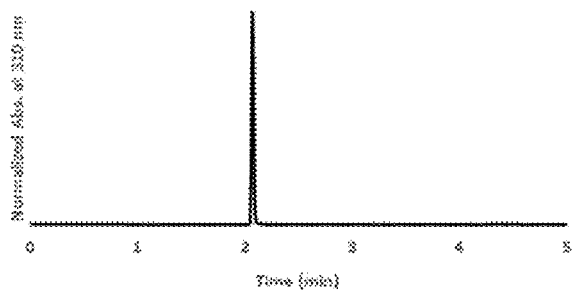
[FIG. 16]
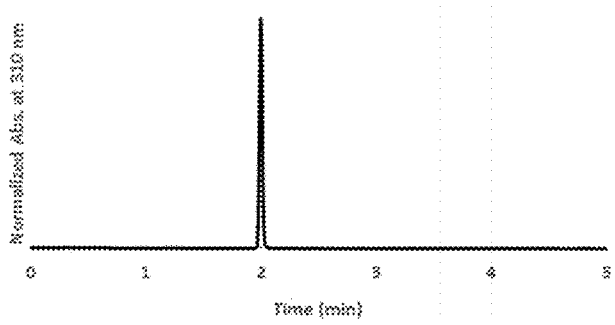

FLUORESCENT PROBE FOR DETECTING CARBOXYPEPTIDASE ACTIVITY

TECHNICAL FIELD

The present invention relates to a novel carboxypeptidase activity-detecting fluorescent probe.

BACKGROUND ART

Carboxypeptidase (CP) is a general term for a group of enzymes that recognizes/cleaves an amino acid residue on a C-terminal side of a peptide chain, it has been reported to be involved in various diseases, and, in addition, has been known to be involved in important biological functions such as cell differentiation.

As carboxypeptidase activity detection fluorescent probes that have heretofore been developed/reported, there is a carboxypeptidase activity-detecting fluorescent probe (Non Patent Literature 1) that utilizes control of spirocyclization equilibrium of rhodamine. This fluorescent probe is the world's first carboxypeptidase activity-detecting fluorescent probe, and is a useful probe that has succeeded in detecting pancreatic fluid leakage in an animal model by detecting activity of carboxypeptidase B. However, since the fluorescent probe has two reaction points, there are problems that sensitivity and quantification are poor and it is difficult to detect the activity in living cells.

In addition, a carboxypeptidase activity-detecting fluorescent probe utilizing characteristic reactivity of an azo-formyl group has also been developed (Japanese Patent Application No. 2018-037791), and this fluorescent probe has advantages that it has one reaction point with carboxypeptidase, a fluorescence increase by 300 times or more is achieved, and activity of PSMA, which has been established as a cancer biomarker can be detected. However, this fluorescent probe has problems that the synthesis is complicated and that an azo group may be reduced by an intracellular reductase.

CITATION LIST

Non Patent Literature

Non Patent Literature 1: Kuriki, Kamiya, Urano et al. JACS, 2018, 140, 1767

SUMMARY OF INVENTION

Technical Problem to be Solved

An object of the present invention is to provide a novel fluorescent probe for detecting carboxypeptidase activity. In particular, an object of the present invention is to provide a carboxypeptidase activity-detecting fluorescent probe showing a large fluorescence intensity change at one reaction point and capable of visualizing the carboxypeptidase activity in living cells with high sensitivity.

Means to Solve the Problem

The present inventors have focused on ProTide chemistry, which is a prodrug technology for introducing a nucleic acid monophosphorylated derivative into a cell, have intensively studied to develop a carboxypeptidase activity-detecting fluorescent probe, capable of showing a large fluorescence intensity change at one reaction point, by applying this technology, and as a result, have completed the present invention.

In other words, the present invention provides:
[1] a compound represented by the following general formula (I) or a salt thereof.

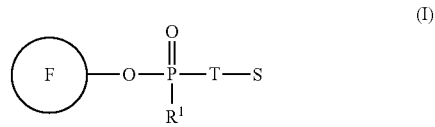

(In the formula,
$R^1$ represents an alkyl group having 1 to 6 carbon atoms or an alkoxy group having 1 to 6 carbon atoms;
T represents an amino acid residue or a residue of an amino acid derivative;
S represents a C-terminal amino acid residue; and

represents a fluorophore, and
the fluorophore is a fluorophore in which an absorption/fluorescence wavelength greatly changes or a quenched state changes to a fluorescent state by elimination of a —P(=O)(—$R^1$)-T-S moiety.)
[2] A carboxypeptidase activity-detecting fluorescent probe comprising the compound or salt thereof according to [1].
[3] A carboxypeptidase detection kit comprising the fluorescent probe according to [2].
[4] A method of detecting activity of carboxypeptidase, the method comprising:
(a) a step of introducing the compound or salt thereof according to [1] into a cell; and
(b) a step of measuring fluorescence emitted when the compound or salt thereof reacts with carboxypeptidase in the cell.
[5] The detection method according to [4], wherein the fluorescence response is visualized using a fluorescence imaging means.

Advantageous Effects of Invention

According to the present invention, it is possible to provide a carboxypeptidase activity-detecting fluorescent probe showing a large fluorescence intensity change at one reaction point and capable of visualizing carboxypeptidase activity in living cells with high sensitivity. The probe of the present invention can detect the carboxypeptidase activity even in ex vivo.

The carboxypeptidase activity-detecting fluorescent probe of the present invention is useful for constructing a system or the like that visualizes/detects a minute cancer site with high sensitivity in surgery.

In addition, the carboxypeptidase activity-detecting fluorescent probe of the present invention can also be effectively used for imaging breast cancer.

BRIEF DESCRIPTION OF DRAWINGS

FIG. 1 illustrates a molecular design of a carboxypeptidase activity-detecting fluorescent probe of the present invention.

FIG. 2 illustrates results of an enzyme assay of Compound A and CPA.

FIG. 3 illustrates results of an enzyme assay of Compound B and CPB.

FIG. 4 illustrates results of an enzyme assay of Compound C and CPB.

FIG. 5 illustrates results of an enzyme assay with HMRef-tSoul-AR.

FIG. 6 illustrates results of live imaging of CPM activity in MDCK cells using HMRef-tSoul-AR.

FIG. 7 illustrates results of UPLC analysis of a medium of the MDCK cells cultured in 20 μM HMRef-tSoul-AR in the presence or absence of 10 μM MGTA.

FIG. 8 illustrates results of an enzyme assay using 4MU-tSoul-AE and PSMA.

FIG. 9 illustrates results of an enzyme assay using 4MU-tSoul-GE and PSMA.

FIG. 10 illustrates results of fluorescence imaging for four specimens derived from breast cancer patients using HMRef-tSoul-AR.

FIG. 11 illustrates the UPLC chromatogram of Compound A.

FIG. 12 illustrates the UPLC chromatogram of Compound B.

FIG. 13 illustrates the UPLC chromatogram of Compound C.

FIG. 14 illustrates the UPLC chromatogram of HMRef-tSoul-AR.

FIG. 15 illustrates the UPLC chromatogram of 4MU-tSoul-AE.

FIG. 16 illustrates the UPLC chromatogram of 4MU-tSoul-GE.

DETAILED DESCRIPTION OF THE PREFERRED EMBODIMENTS

In the present specification, unless otherwise noted, "alkyl group" or an alkyl moiety of a substituent (e.g., alkoxy group) containing the alkyl moiety refers to an alkyl group including a straight chain, branched chain, ring, or combination thereof having, for example, carbon atoms of 1 to 6, preferably carbon atoms of 1 to 4, more preferably carbon atoms of about 1 to 3. More specifically, examples of the alkyl group include a methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group.

In the present specification, the term "halogen atom" may be a fluorine atom, chlorine atom, bromine atom, or iodine atom, and is preferably a fluorine atom, chlorine atom, or bromine atom.

One aspect of the present invention is a compound represented by the following general formula (I), or salt thereof.

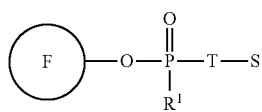
(I)

The present inventors have focused on ProTide chemistry, which is a prodrug technology for introducing a nucleic acid monophosphorylated derivative into a cell, and have developed a carboxypeptidase activity-detecting fluorescent probe by applying this technology. An activation mechanism of ProTide in cells has been studied for many years, and it is currently considered that a monophosphorylated derivative of a target nucleic acid derivative is released through the following process. That is, in this mechanism, a target nucleotide is released through four stages of (1) hydrolysis of an ester by an intracellular esterase such as Cathepsin A or carboxylesterase, (2) intramolecular cyclization reaction by nucleophilic attack of the resulting carboxylate on phosphorus and the accompanying elimination of an aryloxy group, (3) hydrolysis of a five-membered ring structure generated by intramolecular cyclization, and (4) metabolism by a phosphoramidase-type enzyme.

In the present invention, attention is paid to the first stage and the second stage in this activation. That is, although ProTide generates carboxylate using an intracellular esterase as a trigger and releases a phenol derivative by the intramolecular cyclization reaction, this trigger is changed to carboxypeptidase, and a probe is designed so that a fluorophore is released by the intramolecular cyclization reaction, so that a carboxypeptidase activity-detecting fluorescent probe has been developed (see FIG. 1).

In the general formula (I), $R^1$ represents an alkyl group having 1 to 6 carbon atoms or an alkoxy group having 1 to 6 carbon atoms. $R^1$ is preferably an alkyl group having 1 to 6 carbon atoms, and particularly preferably a t-butyl group or an isopropyl group. By introducing these groups having a large steric hindrance, such as a t-butyl group, as $R^1$ onto a phosphorus atom, non-enzymatic hydrolysis, for example, nucleophilic attack of a water molecule on a phosphate group can be suppressed.

In the general formula (I), T is a moiety having a —NH—CRR'—C(=O)— structure, and examples thereof include general α-amino acid residues (glycine, alanine, leucine, isoleucine, valine, lysine, cysteine, threonine, arginine, asparagine, aspartic acid, glutamine, glutamic acid, serine, histidine, phenylalanine, methionine, tryptophan, tyrosine, proline) and residues of derivatives thereof (N-methylleucine, 2,3-diaminopropanoic acid, 2,4-diaminobutyric acid, ornithine, α-hydroxyleucine, and the like). The amino acid residue and the derivative thereof may be either an L-form amino acid or a D-form amino acid residue.

The amino acid residue is preferably glycine or alanine.

In one aspect of the present invention, T is represented by the following formula (1).

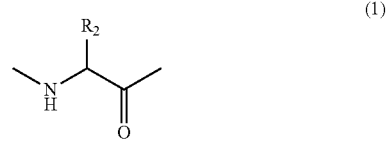
(1)

In the formula (1), $R^2$ represents a group constituting a side chain of a natural amino acid (glycine, alanine, leucine, isoleucine, valine, lysine, cysteine, threonine, arginine, asparagine, aspartic acid, glutamine, glutamic acid, serine, histidine, phenylalanine, methionine, tryptophan, tyrosine, proline), such as hydrogen, a methyl group or the like. $R^2$ also includes a group other than the group constituting the side chain of the natural amino acid, for example, an alkyl group having various substituents.

NH in the formula (1) is bonded to P.

In the general formula (I), S represents a C-terminal amino acid residue. The amino acid residue of S is selected from residues of glycine, alanine, leucine, isoleucine, valine, lysine, cysteine, threonine, arginine, asparagine, aspartic acid, glutamine, glutamic acid, serine, histidine, phenylalanine, methionine, tryptophan, tyrosine, and proline. The type of the C-terminal amino acid residue of S is selected according to the type of carboxypeptidase, and examples thereof include phenylalanine, arginine, and glutamic acid.

The amino acid residue of S may be either an L-form amino acid or a D-form amino acid residue.

In one aspect of the present invention, S is represented by the following formula (2).

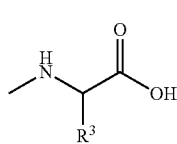

(2)

In the formula (2), $R^3$ represents a group constituting a side chain of a natural amino acid (glycine, alanine, leucine, isoleucine, valine, lysine, cysteine, threonine, arginine, asparagine, aspartic acid, glutamine, glutamic acid, serine, histidine, phenylalanine, methionine, tryptophan, tyrosine, proline), such as hydrogen, a methyl group or the like.

In the general formula (I),

represents a fluorophore.

The fluorophore that can be used in the present invention is a fluorophore in which when the compound or salt thereof according to the present invention reacts with carboxypeptidase, an absorption/fluorescence wavelength greatly changes, or a quenched state changes to a fluorescent state. Specifically, the fluorophore in the present invention is a fluorophore in which the absorption wavelength greatly changes, a fluorescence emission wavelength greatly changes, or the quenched state changes to the fluorescent state by elimination of a —P(=O)(—R$^1$)-T-S moiety by an enzymatic reaction with carboxypeptidase, and any fluorophore having such characteristics can be used without particular limitation.

Examples of such a fluorophore include an absorption/fluorescence wavelength change type fluorophore represented by the following formulas (3) to (5) and a fluorescence intensity change type fluorophore represented by the formula (6).

In one aspect of the present invention, the fluorophore of the general formula (I) is an absorption/fluorescence wavelength change type fluorophore represented by the following formula (3).

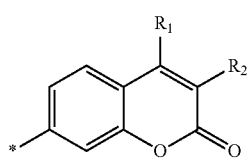

(3)

In the formula (3), $R_1$ represents hydrogen or an alkyl group having 1 to 6 carbon atoms.

In the formula (3), $R^2$ represents hydrogen, a carboxyl group, or an ester group (—COOR: R represents an alkyl group having 1 to 6 carbon atoms).

In the formula (3), * represents a moiety bonded to —O—P(=O)(—R$^1$)-T-S.

In one aspect of the present invention, one non-limiting example of a fluorophore represented by the formula (3) is 4-methylumbelliferone (4MU) represented by the following formula.

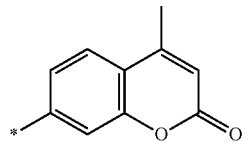 [SMILES: *c1ccc2c(C)cc(=O)oc2c1]

In one aspect of the present invention, the fluorophore of the general formula (I) is an absorption/fluorescence wavelength change type fluorophore represented by the following formula (4).

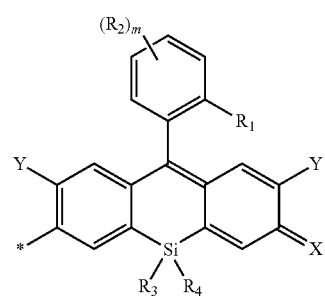

(4)

In the formula (4), $R_1$ represents a hydrogen atom, an alkyl group having 1 to 6 carbon atoms, an alkoxyl group having 1 to 6 carbon atoms, or a carboxyl group.

In the formula (4), $R_2$, when present, represents the same or different monovalent substituents present on the benzene ring. Examples of the monovalent substituent include an alkyl group having 1 to 6 carbon atoms, an alkoxyl group having 1 to 6 carbon atoms, and a carboxyl group.

m is an integer of 0 to 4. When m is 2 or more, each $R_2$ may be the same or different.

In the formula (4), Y each independently represents a hydrogen atom, an alkyl group having 1 to 6 carbon atoms, or a halogen atom.

In the formula (4), $R_3$ and $R_4$ each independently represent an alkyl group or aryl group having 1 to 6 carbon atoms, preferably, $R_3$ and $R_4$ are each independently an alkyl group having 1 to 3 carbon atoms, and more preferably, both $R_3$ and $R_4$ are a methyl group. One or more halogen atoms, carboxy groups, sulfonyl groups, hydroxy groups, amino groups, alkoxy groups, or the like may be present in the alkyl group represented by $R^3$ and $R^4$, and, for example, the alkyl group represented by $R^3$ or $R^4$ may be an alkyl halide group, a hydroxyalkyl group, a carboxyalkyl group, or the like.

When $R_3$ and $R_4$ represent an aryl group, the aryl group may be a monocyclic aromatic group or condensed aromatic group, and the aryl ring may include one or more ring-structured heteroatoms (e.g., nitrogen atom, oxygen atom, sulfur atom, or the like). A phenyl group is preferred as the aryl group. One or more substituent groups may be present on the aryl ring. One or more substituent groups such as a halogen atom, carboxy group, sulfonyl group, hydroxy group, amino group, alkoxy group, or the like may be present.

In the formula (4), X is an oxygen atom or NR (R represents a hydrogen atom or a substituted or unsubstituted alkyl group having 1 to 6 carbon atoms, and examples thereof include a fluorinated alkyl group (for example, —$CH_2$—$CF_3$, —$CH_2$—$CH_2$—$CF_3$)).

In the formula (4), * represents a moiety bonded to —O—P(=O)(—$R^1$)-T-S.

In one aspect of the present invention, the fluorophore of the general formula (I) is an absorption/fluorescence wavelength change type fluorophore represented by the following formula (5).

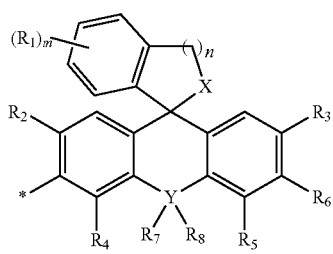

(5)

In the formula (5), $R^1$, when present, represents the same or different monovalent substituents present on the benzene ring. Examples of the monovalent substituent include an alkyl group having 1 to 6 carbon atoms, an alkoxyl group having 1 to 6 carbon atoms, and a carboxyl group.

m is an integer of 0 to 4. When m is 2 or more, each $R_2$ may be the same or different.

In a preferred aspect of the present invention, m is 0.

In the formula (5), $R_2$ and $R_3$ are each independently a hydrogen atom, an alkyl group having 1 to 6 carbon atoms, or a halogen atom.

When $R^2$ or $R_3$ represents an alkyl group, one or more halogen atoms, carboxy groups, sulfonyl groups, hydroxy groups, amino groups, alkoxy groups, or the like may be present in the alkyl group, and, for example, the alkyl group represented by $R_2$ or $R_3$ may be an alkyl halide group, a hydroxyalkyl group, a carboxyalkyl group, or the like. $R^2$ and $R^3$ are preferably each independently a hydrogen atom or a halogen atom. When $R_2$ and $R_3$ are halogen atoms, it is more preferable that $R_2$ and $R_3$ are both fluorine atoms or chlorine atoms.

In a preferred aspect of the present invention, $R_2$ and $R^3$ are hydrogen atoms.

In the formula (5), $R_4$ and $R^5$ are each independently a hydrogen atom, an alkyl group having 1 to 6 carbon atoms, or a halogen atom, and are the same as those described for $R^2$ and $R^3$. It is preferable that both $R_4$ and $R_5$ are a hydrogen atom.

In the formula (5), $R_6$ is selected from NH2, NHR, NRR', OH, or OR". R and R' each independently represent an alkyl group having 1 to 5 carbon atoms or a fluoroalkyl group having 1 to 5 carbon atoms. R" represents an alkyl group having 1 to 5 carbon atoms. Here, the alkyl group is preferably a methyl group or an ethyl group. The fluoroalkyl group is preferably —$CH_2$—$CF_3$ or —$CH_2$—$CH_2$—$CF_3$.

In the formula (5), $R_7$ and $R_8$, when present, each independently represent an alkyl group or aryl group having 1 to 6 carbon atoms, preferably, $R_7$ and $R_8$ are each independently an alkyl group having 1 to 3 carbon atoms, and more preferably, both $R_7$ and $R_8$ are a methyl group. One or more substituents such as halogen atoms, carboxy groups, sulfonyl groups, hydroxy groups, amino groups, alkoxy groups, or the like may be present in the alkyl group represented by $R_7$ and $R_8$, and, for example, the alkyl group represented by $R_7$ or $R_8$ may be an alkyl halide group, a hydroxyalkyl group, a carboxyalkyl group, or the like.

When $R_7$ and $R_8$ represent an aryl group, the aryl group may be a monocyclic aromatic group or condensed aromatic group, and the aryl ring may include one or more ring-structured heteroatoms (e.g., nitrogen atom, oxygen atom, sulfur atom, or the like). A phenyl group is preferred as the aryl group. One or more substituent groups may be present on the aryl ring. One or more substituent groups such as a halogen atom, carboxy group, sulfonyl group, hydroxy group, amino group, alkoxy group, or the like may be present.

When Y described later is an oxygen atom, $R_7$ and $R_8$ are not present.

Furthermore, when Y described later is a phosphorus atom, one of $R_7$ and $R_8$ is =O.

In the formula (5), X represents an oxygen atom or NRa. Here, Ra represents a hydrogen atom or an alkyl group having 1 to 5 carbon atoms.

Y represents an oxygen atom, a silicon atom, a carbon atom, or a phosphorus atom.

In a preferred aspect of the present invention, Y is an oxygen atom.

n is an integer of 1 to 3, and is preferable to be 1.

In the formula (5), * represents a moiety bonded to —O—P(=O)(—$R^1$)-T-S.

In one aspect of the present invention, the fluorophore of the general formula (I) is a fluorescence intensity change type fluorophore represented by the following formula (6).

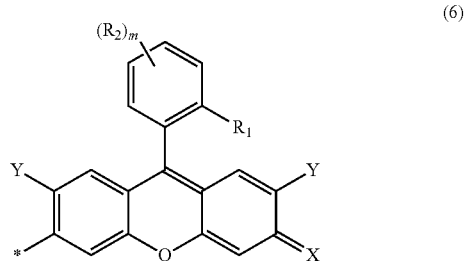

(6)

In the formula (6), $R_1$ represents a hydrogen atom, an alkyl group having 1 to 6 carbon atoms, an alkoxyl group having 1 to 6 carbon atoms, or a carboxyl group.

In the formula (6), $R^2$, when present, represents the same or different monovalent substituents present on the benzene ring. Examples of the monovalent substituent include an alkyl group having 1 to 6 carbon atoms, an alkoxyl group having 1 to 6 carbon atoms, and a carboxyl group.

m is an integer of 0 to 4. When m is 2 or more, each $R_2$ may be the same or different.

In a preferred aspect of the present invention, m is 0.

In the formula (6), Y each independently represents a hydrogen atom, an alkyl group having 1 to 6 carbon atoms, or a halogen atom.

In the formula (6), X is an oxygen atom or NR (R represents a hydrogen atom or a substituted or unsubstituted alkyl group having 1 to 6 carbon atoms, and examples thereof include a fluorinated alkyl group (for example, —CH$_2$—CF$_3$, —CH$_2$—CH$_2$—CF$_3$)).

In the formula (6), * represents a moiety bonded to —O—P(=O)(—R$^1$)-T-S.

One aspect of the present invention is a compound represented by the following general formula (II), or salt thereof.

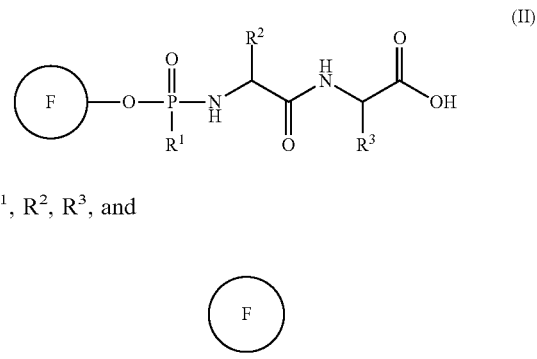

R$^1$, R$^2$, R$^3$, and in the general formula (II) are the same as those described regarding the general formula (I).

The compounds represented by the general formulas (I) and (II) of the present invention can exist as acid addition salts or base addition salts. Examples of the acid addition salt include mineral acid salts such as hydrochlorides, sulfates and nitrates, and organic acid salts such as methanesulfonate, p-toluenesulfonate, oxalate, citrate and tartrate. Examples of the base addition salt include metal salts such as sodium salt, potassium salt, calcium salt and magnesium salt, ammonium salt, and organic amine salts such as triethylamine salt. In addition to these, there are also cases in which salts are formed with an amino acid such as glycine. Compounds or salts thereof according to the present invention can also exist as hydrates or solvates, but these substances are also within the scope of the present invention.

The compounds represented by the general formulas (I) and (II) of the present invention sometimes have one or more asymmetrical carbons, depending on the types of substituents. In addition to optical isomers based on one or more asymmetrical carbons and stereoisomers such as diastereomers based on two or more asymmetrical carbons, any mixtures of stereoisomers, racemates, etc., are all encompassed within the scope of the present invention.

Methods for producing representative compounds of compounds of the present invention are specifically shown in the examples in the present specification. Therefore, one skilled in the art can produce the compound of the present invention represented by general formula (I) by appropriately selecting the reaction raw materials, reaction conditions, reaction reagents, etc. based on these explanations and modifying or changing these methods as needed.

The compounds of the present invention represented by the general formulas (I) and (II) of the present invention are useful as fluorescent probes that detect carboxypeptidase activity.

That is, another aspect of the present invention is a fluorescent probe including the compound represented by the general formula (I) or salt thereof.

In addition, another aspect of the present invention is a method of detecting the carboxypeptidase activity in cells, the method including (a) a step of introducing the compound represented by the general formula (I) or salt thereof into a cell, and (b) a step of measuring fluorescence emitted when the compound or salt thereof reacts with carboxypeptidase in the cell.

The compound of the present invention represented by the general formula (I) or salt thereof is substantially non-fluorescent or has only weak fluorescence in environments free of carboxypeptidase, but emits strong fluorescence in environments where carboxypeptidase is present.

The method of the present invention can further include observing a fluorescence response using a fluorescence imaging means. Although a fluorometer having a wide measurement wavelength can be used as a means for observing the fluorescence response, the fluorescence response can also be visualized using a fluorescence imaging means that can display the fluorescence response as a two-dimensional image. Since the fluorescence response can be visualized two-dimensionally by using the fluorescence imaging means, it becomes possible to instantly recognize carboxypeptidase. Devices known in the art can be used as the fluorescence imaging device. The reaction of the sample to be measured and the fluorescent probe can also be detected in some cases by a change in an UV-visible absorption spectrum (for example, a change in absorbance at a specific absorption wavelength).

The method of using the fluorescent probe of the present invention is not particularly limited, and the fluorescent probe can be used in the same manner as conventionally known fluorescent probes. Usually, the compound represented by the above formula (I) or salt thereof may be dissolved in an aqueous medium such as physiological saline and buffer, a mixture of the aqueous medium and a water-miseible organic solvent such as ethanol, acetone, ethylene glycol, dimethyl sulfoxide, and dimethylformamide, or the like, this solution may be added to an appropriate buffer containing cells or tissues, and fluorescence spectrum may be measured. The fluorescent probe of the present invention may be combined with an appropriate additive and used in the form of a composition. For example, the fluorescent probe may optionally be combined with additives such as buffers, dissolving aids, and pH adjusting agents.

Examples of carboxypeptidase that can be detected by the fluorescent probe of the present invention include various carboxypeptidases such as carboxypeptidase A, carboxypeptidase B, carboxypeptidase M, and Prostate specific membrane antigen (PSMA), but are not limited thereto.

Although the sample of cells to be measured in the step (a) can be cells expressing carboxypeptidase, when such cells are cancer cells or cancer tissues expressing carboxypeptidase, the cancer cells or the cancer tissues can be detected or visualized by the detection method according to the present invention. That is, the fluorescent probe of the present invention, a composition containing the fluorescent probe, and the detection method according to the present invention can also be used for diagnosis of cancer.

In the present specification, the term "cancer tissue" means any tissue comprising cancer cells. The term "tissue" must be interpreted in the broadest sense, comprising all or part of an organ, and must not be interpreted restrictively in any sense. Tissues that express a high level of carboxypeptidase are preferred as cancer tissues. Also, the term "diagnosis" in the present specification must be interpreted in the broadest sense, including confirmation of cancer tissue at any site in the body visually or under a microscope.

In a preferred aspect of the detection method according to the present invention, the sample of cells to be measured in the step (a) is a cancer cell, preferably a breast cancer cell.

In the detection method according to the present invention, it is preferable to use a carboxypeptidase detection kit including the fluorescent probe. In the kit, the fluorescent probe of the present invention is usually prepared as a solution, but the fluorescent probe of the present invention can also be provided as a composition of a suitable form such as mixture in powdered form, freeze-dried product, granules, tablets, liquid, or the like and used by being dissolved in distilled water for injection or a suitable buffer at the time of use.

In addition, the kit may also appropriately include reagents or the like other than them, as needed. For example, dissolution auxiliaries, pH adjusters, buffers, isotonifying agents, and other such additives can be used as additives, and the amounts compounded can be selected as is appropriate by one skilled in the art.

EXAMPLES

Hereinafter, the present invention is described by Examples, but the present invention is not limited thereto.
[Raw Materials]
All chemical substances used in synthesis were purchased from Tokyo Chemical Industry Co., Ltd., Wako Pure Chemical Industries, Ltd., and Sigma-Aldrich Co. LLC. The substances were used without further purification.
[Measuring Instrument]
An NMR spectrum was obtained in a deuterated solvent with JEOL JNM-LA400 [$^1$H 400 MHz, $^{13}$C 100 MHz] or Bruker NMR AVANCE III 400 spectrometer [31P (162 MHz)].

High-resolution ESI mass spectra were obtained with JEOL JMS-T100LC AccuToF (ESI).

HPLC purification was performed with a JASCO PU-2080 Plus pump (GL Science Co., Ltd.) and an MD-2015 detector (JASCO) equipped with an Inertstil-ODS-3 column ((10×250 mm (semi-preparative) and T 20×250 mm (preparative)).

The solvent used for HPLC was obtained from Wacoh Corporation. Silica gel column chromatography was performed using silica gel 60N (spherical, neutral, 63 to 210 μm; manufactured by Kanto Chemical Co., Inc.).

TLC was performed on silica gel plate F254 (0.25 mm (analysis); Merck, AKG).

A UV-vis spectrum was obtained with a Shimadzu UV-1800 spectrophotometer.

A fluorescence spectrum was acquired with F-7100 (Hitachi).

Synthesis Example 1

4-MU having blue fluorescence as a fluorophore, and Compounds A and B having an alanine residue as T, an ethoxy group as $R^1$, and a phenylalanine residue and an arginine residue as S, respectively, in the general formula (I) were synthesized. Although a diastereomer was present in the present molecular design including Compounds A and B, these were not isolated, and evaluation was performed using a mixture.

In the synthesis, 4-MU and a separately prepared dipeptide (2, 3) were sequentially condensed with respect to ethyl dichlorophosphate (1) according to the following Scheme 1, and a protecting group was then removed under acidic conditions to obtain a target compound.

Scheme 1

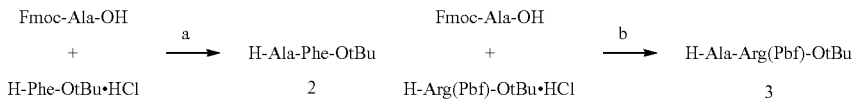

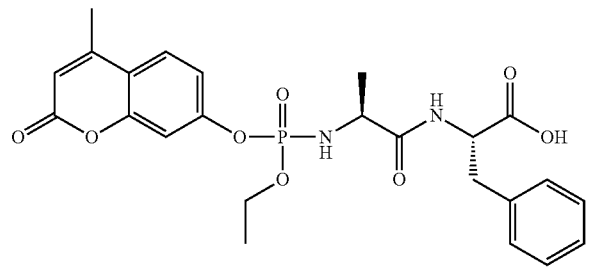

Compound A

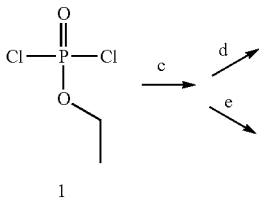

1

-continued

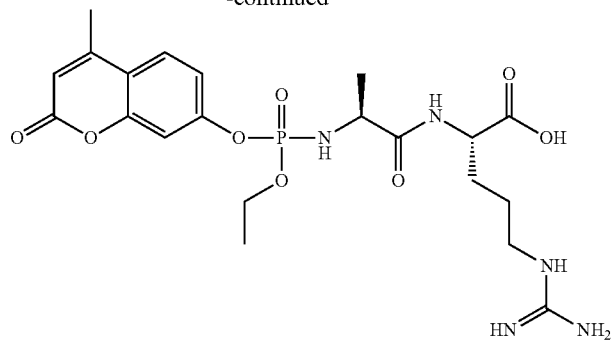

Compound B (a) 1) HATU, DIEA, DMF, 2) Piperidine, DMF, y. 85% in 2 steps. (b) 1) 1) HATU, DIEA, DMF, 2) Piperidine, DMF, y. 71% in 2 steps. (c) 4-MU, TEA, THF, (d) 1) H-Ala-Phe-OtBu TEA, THF, 2) TFA, MeCN, y. 8.4% in 3 steps, diastereomer mixture (e) 1) H-Ala-Arg(Pbf)-OtBu, TEA, THF, 2) TFA, MeCN, y. 17% in 3 steps, diastereomer mixture Synthesis of Compound 2

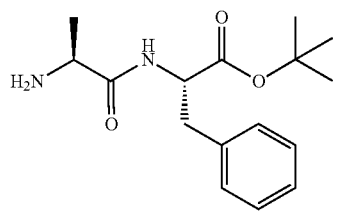 [SMILES: C[C@H](N)C(=O)N[C@@H](Cc1ccccc1)C(=O)OC(C)(C)C]

Fmoc-Ala-OH (622 mg, 2.00 mmol), H-Phe-OtBu hydrochloride (515 mg, 2.00 mmol) and N, N-diisopropylethylamine (1032 μL, 5.92 mmol) were dissolved in 5 mL of N, N-dimethylformamide, HATU (837 mg, 2.20 mmol) was added thereto, and the mixture was stirred at room temperature overnight. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was dissolved in 8 mL of N, N-dimethylformamide, 2 mL of piperidine was added thereto, and the mixture was stirred at room temperature overnight. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was purified by aminosilica gel column chromatography (ethyl acetate/hexane=1/2→2/1) to obtain Compound 2 (498 mg, 85%).

$^1$H NMR (400 MHz, CDCl$_3$): δ 1.25 (d, J=6.9 Hz, 3H), 1.41 (s, 9H), 3.21-2.99 (m, 2H), 3.46 (q, J=7.0 Hz, 1H), 4.82-4.64 (m, 1H), 7.19-7.13 (m, 2H), 7.36-7.19 (m, 3H), 7.65 (d, J=7.8 Hz, 1H)

$^{13}$C NMR (100 MHz, CDCl$_3$): δ 21.7, 28.0, 38.3, 50.8, 53.1, 82.2, 126.9, 128.3, 129.6, 136.4, 170.9, 175.3

HRMS (ESI$^+$): calcd for [M+H]$^+$, 293.18652; found, 293.18572 (−0.89 mmu)

Synthesis of Compound 3

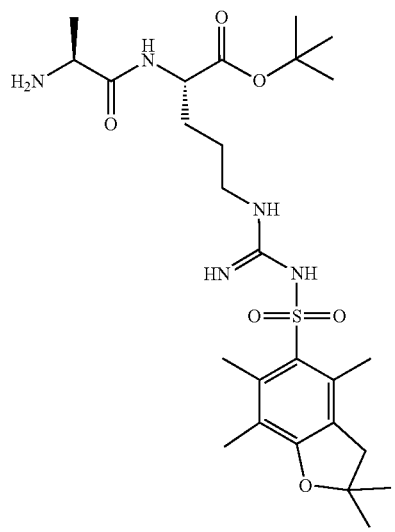 [SMILES: Cc1c(C)c(S(=O)(=O)NC(=N)NCCC[C@H](NC(=O)[C@H](C)N)C(=O)OC(C)(C)C)c(C)c2c1OC(C)(C)C2]

Fmoc-Ala-OH (595 mg, 1.91 mmol), H-Arg(Pbf)-OtBu hydrochloride (992 mg, 1.91 mmol) and N, N-diisopropylethylamine (986 μL, 5.73 mmol) were dissolved in 15 mL of N, N-dimethylformamide, and HATU (799 mg, 2.10 mmol) was added and stirred at room temperature for 1 hour. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was dissolved in 8 mL of N, N-dimethylformamide, 2 mL of piperidine was added thereto, and the mixture was stirred at room temperature for 90 minutes. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was purified by aminosilica gel column chromatography (dichloromethane→dichloromethane/methanol=95/5) to obtain Compound 3 (745 mg, 71%).

$^1$H NMR (400 MHz, CD$_3$OD): δ 1.25 (d, J=6.9 Hz, 3H), 1.43 (s, 9H), 1.45 (s, 6H), 1.49-1.61 (m, 2H), 1.61-1.72 (m,

1H), 1.72-1.96 (m, 1H), 2.07 (s, 3H), 2.50 (s, 3H), 2.57 (s, 3H), 2.99 (s, 2H), 3.07-3.25 (m, 2H), 3.45 (q, J=6.9 Hz, 1H), 4.23 (dd, J=5.0, 8.2 Hz, 1H)

$^{13}$C NMR (100 MHz, CD$_3$OD): δ 11.2, 17.1, 18.3, 20.3, 25.6, 26.9, 27.4, 28.6, 40.2, 42.6, 49.9, 52.7, 81.6, 86.3, 117.1, 124.7, 132.1, 133.1, 138.0, 156.7, 158.5, 171.2, 177.1

HRMS (ESI$^+$): calcd for [M+H]$^+$, 554.30123; found, 554.30128 (0.05 mmu)

Synthesis of Compound A

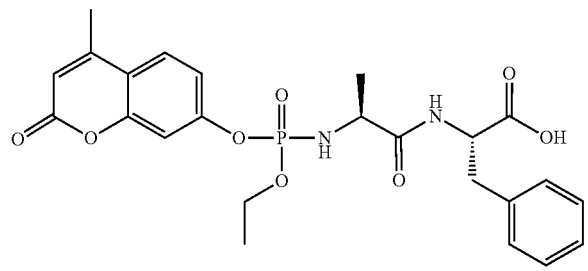 [SMILES: CCOP(=O)(N[C@@H](C)C(=O)N[C@@H](Cc1ccccc1)C(=O)O)Oc1ccc2c(C)cc(=O)oc2c1]

Ethyl phosphorodichloridate (21 μL, 0.171 mmol) was dissolved in 1.5 mL of tetrahydrofuran and stirred under an argon atmosphere at −78° C. for 10 minutes. 4-Methylumbelliferone (31 mg, 0.171 mmol) and triethylamine (47 μL, 0.342 mmol) dissolved in 1 mL of tetrahydrofuran were sequentially and slowly added dropwise, then the temperature was raised to room temperature, and the mixture was stirred under an argon atmosphere for 2 hours. The reaction solution was stirred again at −78° C. for 10 minutes, then Compound 2 (100 mg, 0.342 mmol) dissolved in 1 mL of tetrahydrofuran and triethylamine (94 μL, 0.684 mmol) were sequentially and slowly added dropwise, then the temperature was raised to room temperature, and the mixture was stirred overnight under an argon atmosphere. After the reaction was stopped by adding water, an aqueous layer was extracted using dichloromethane and ethyl acetate, the combined organic layers were dried using sodium sulfate, and the solvent was removed under reduced pressure. The residue was partially purified by silica gel column chromatography (ethyl acetate). After collecting a fraction containing the target compound, the solvent was removed by removal under reduced pressure, the residue was dissolved in 1 mL of acetonitrile, then 3 mL of trifluoroacetic acid was added, and the mixture was stirred at room temperature for 2 hours. The residue obtained by removing the solvent under reduced pressure was purified by HPLC (eluent A (H$_2$O 0.1% TFA) and eluent B (CH$_3$CN 80%, H$_2$O 20%, 0.1% TFA) (A/B=80/20 to 0/100 in 30 min)) to obtain a target compound (7.2 mg, 8.4%).

$^1$H NMR (400 MHz, DMSO-d6): δ 1.26-1.03 (m, 6H), 2.41 (d, J=1.4 Hz, 3H), 2.95-2.76 (m, 1H), 3.14-2.95 (m, 1H), 3.84-3.65 (m, 1H), 4.11-3.84 (m, 2H), 4.53-4.30 (m, 1H), 5.90-5.66 (m, 1H), 6.34 (s, 1H), 7.32-7.03 (m, 7H), 7.73 (dd, J=11.9, 8.7 Hz, 1H), 8.06 (d, J=7.8 Hz, 1H)

$^{13}$C NMR (100 MHz, DMSO-d6): δ 16.4 (d, J=6.7 Hz), 16.5 (d, J=6.7 Hz), 18.7, 21.1, 21.2, 21.3, 37.2, 50.8 (d, J=4.8 Hz), 53.7, 53.8, 63.0 (d, J=4.8 Hz), 63.1 (d, J=5.7 Hz), 108.3 (d, J=5.7 Hz), 108.5 (d, J=4.8 Hz), 113.6, 116.8 (containing 2 peaks), 117.0 (d, J=4.8 Hz), 117.2 (d, J=5.7 Hz), 126.9, 127.0, 127.2, 128.6, 128.7, 129.6, 137.8, 153.5, 153.9 (d, J=5.8 Hz), 154.0 (d, J=6.7 Hz), 154.2, 154.3, 160.2, 173.2 (containing 2 peaks)

$^{31}$P NMR (162 MHz, DMSO-d6): δ 3.55, 3.89

HRMS (ESI$^+$): calcd for [M+H]$^+$, 503.15833; found, 503.15702 (−1.31 mmu)

The UPLC (eluent; A/B=95/5 to 5/95 in 4 min) chromatogram after purification is shown. Absorbance at 310 nm was detected. Eluent A (H2O containing 0.1% formic acid) and eluent B (80% acetonitrile and 20% H2O containing 0.1% formic acid) were used for UPLC analysis.

Synthesis of Compound B

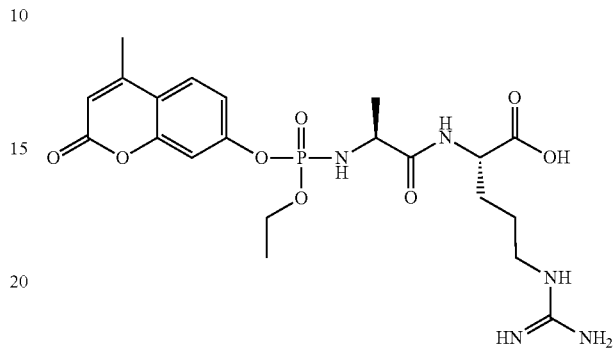

Ethyl phosphorodichloridate (21 μL, 0.171 mmol) was dissolved in 1.5 mL of tetrahydrofuran and stirred under an argon atmosphere at −78° C. for 10 minutes. 4-Methylumbelliferone (31 mg, 0.171 mmol) and triethylamine (47 μL, 0.342 mmol) dissolved in 1 mL of tetrahydrofuran were sequentially and slowly added dropwise, then the temperature was raised to room temperature, and the mixture was stirred under an argon atmosphere for 2 hours. The reaction solution was stirred again at −78° C. for 10 minutes, then Compound 3 (189 mg, 0.341 mmol) dissolved in 1 mL of tetrahydrofuran and triethylamine (94 μL, 0.684 mmol) were sequentially and slowly added dropwise, then the temperature was raised to room temperature, and the mixture was stirred overnight under an argon atmosphere. After the reaction was stopped by adding a saturated aqueous ammonium chloride solution, an aqueous layer was extracted using dichloromethane and ethyl acetate, the combined organic layers were dried using sodium sulfate, and the solvent was removed under reduced pressure. The residue was partially purified by silica gel column chromatography (ethyl acetate→ethyl acetate/methanol=97/3). After collecting a fraction containing the target compound, the solvent was removed by removal under reduced pressure, 3 mL of trifluoroacetic acid was added to the residue, and the mixture was stirred at room temperature for 1 hour. The residue obtained by removing the solvent under reduced pressure was partially purified by HPLC (eluent A (H$_2$O 0.1% TFA) and eluent B (CH$_3$CN 80%, H$_2$O 20%, 0.1% TFA) (A/B=80/20 to 0/100 in 30 min)). After collecting a fraction containing the target compound, the solvent was removed by removal under reduced pressure, and the residue was partially purified by HPLC (eluent C (H$_2$O containing 100 mM triethylammonium acetate) and eluent D (80% acetonitrile and 20% H$_2$O containing 100 mM triethylammonium acetate) (C/D=80/20 to 0/100 in 30 min)). After collecting a fraction containing the target compound, the solvent was removed by removal under reduced pressure, the residue was generated again by HPLC (eluent A (H$_2$O 0.1% TFA) and eluent B (CH$_3$CN 80%, H$_2$O 20%, 0.1% TFA) (A/B=80/20 to 0/100 in 30 min)) to obtain a target compound (18 mg, 17%).

$^1$H NMR (400 MHz, DMSO-d6+D$_2$O): δ 1.09-1.24 (m, 6H), 1.32-1.47 (m, 2H), 1.47-1.62 (m, 1H), 1.62-1.78 (m,

1H), 2.37 (s, 3H), 2.92-3.12 (m, 2H), 3.71-3.82 (m, 1H), 4.07-4.22 (m, 1H), 6.29 (s, 1H), 7.06-7.25 (m, 2H), 7.40-7.57 (m, 1H), 7.64-7.81 (m, 1H), 8.09 (d, J=7.8 Hz, 1H)

$^{13}$C NMR (100 MHz, DMSO-d6): δ 16.4, 16.5 (containing 2 peaks), 18.7, 21.2, 21.3, 25.5, 25.6, 28.8, 40.8, 50.7 (containing 2 peaks), 52.0, 63.1 (containing 2 peaks), 63.2, 108.3 (d, J=4.8 Hz), 108.5 (d, J=4.8 Hz), 113.6, 116.8, 116.9, 117.1 (d, J=5.8 Hz), 117.3 (d, J=5.8 Hz), 127.1, 127.2, 153.6, 154.0 (d, J=6.7 Hz), 154.2, 154.3, 157.2, 160.3, 173.4, 173.5 (containing 2 peaks), 173.7 (containing 2 peaks)

$^{31}$P NMR (162 MHz, DMSO-d6): δ 3.62, 4.00

HRMS (ESI$^+$): calcd for [M+H]$^+$, 512.19102; found, 512.19088 (−0.15 mmu)

The UPLC (eluent; A/B=95/5 to 5/95 in 4 min) chromatogram after purification is shown. Absorbance at 310 nm was detected. Eluent A (H$_2$O containing 0.1% formic acid) and eluent B (80% acetonitrile and 20% H$_2$O containing 0.1% formic acid) were used for UPLC analysis.

Example 1

An enzyme assay using the synthesized Compounds A, B was performed. As a result, the fluorescence of Compounds A and B was increased by incubation with carboxypeptidase A (CPA) and carboxypeptidase B (CPB) which were the respective target enzymes, and the increase in fluorescence was suppressed by addition of (S)-benzylsuccinic acid and MGTA which were the respective inhibitors. In the enzyme assay of Compound A, since trypsin coexisted for activation of proCPA, although a condition of adding only trypsin was also examined, a remarkable increase in fluorescence was not observed. On the other hand, the fluorescence gradually increased even slightly in the absence of an enzyme, and it was revealed that the present probe underwent a non-enzymatic degradation reaction (FIGS. 2 and 3).

FIG. 2(a) illustrates a reaction scheme of Compound A and CPA. In FIG. 2(b), 10 μM Compound A in PBS (-) was incubated at 37° C. with 5 ng CPA activated by 1.5 μg trypsin in the presence or absence of 100 μM inhibitor ((S)-benzylsuccinic acid) containing 0.1% DMSO as a co-solvent. Ex/Em=355/460 nm. n=4. (In FIG. 2, Try represents trypsin, and SBSA represents (S)-benzylsuccinic acid.)

FIG. 3(a) illustrates a reaction scheme of Compound B and CPB. In FIG. 3(b), 10 μM Compound B in PBS (-) was incubated at 37° C. with 5 ng CPB in the presence or absence of 100 μM inhibitor (MGTA) containing 0.1% DMSO as a co-solvent. Ex/Em=355/460 nm. n=4.

The above results indicate that the present molecular design utilizing ProTide chemistry functions as a new carboxypeptidase activity-detecting fluorescent probe. On the other hand, a non-enzymatic degradation reaction was observed in both probes, and it became clear that stability in an aqueous solution needed to be improved for development of a practical probe.

As a mechanism of the non-enzymatic decomposition reaction of the probe, hydrolysis by nucleophilic attack of a solvent water molecule on a phosphorus atom is considered. As an improvement of the probe for preventing this, improvement of stability due to steric hindrance by changing a substituent on the phosphorus atom to a bulky one was examined.

Synthesis Example 2

Next, a tBu group was newly introduced as a substituent on the phosphorus atom, and Compound C having arginine as the amino acid of S of the general formula (I) was synthesized by the following scheme.

Scheme 2

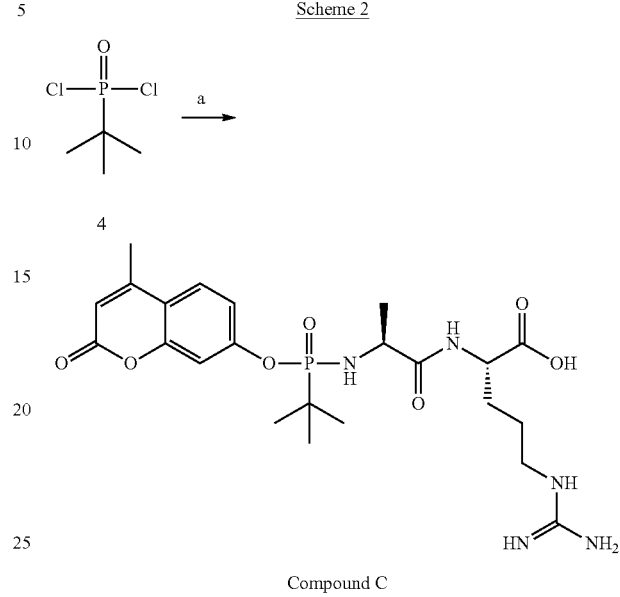

Compound C (a) 1) 4-MU, TEA, THF, 2) H-Ala-Arg(Pbf)-OtBu, TEA, THF, 3) TFA, MeCN, 14% in 3 steps (diastereomer mixture).

Synthesis of Compound C

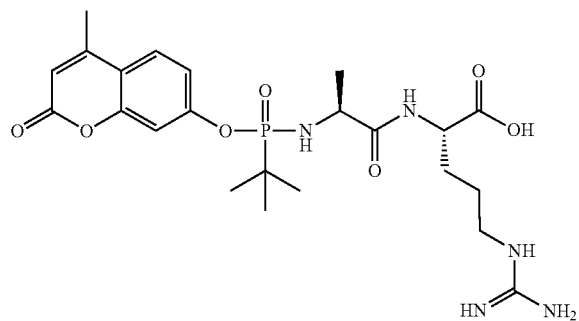 [SMILES: Cc1cc(=O)oc2cc(OP(=O)(N[C@@H](C)C(=O)N[C@@H](CCCNC(=N)N)C(=O)O)C(C)(C)C)ccc12]

tert-Butylphosphonic acid dichloride (30 mg, 0.171 mmol) was dissolved in 1 mL of tetrahydrofuran, and the solution was stirred at −78° C. for 10 minutes under an argon atmosphere. 4-Methylumbelliferone (31 mg, 0.171 mmol) and triethylamine (47 μL, 0.342 mmol) dissolved in 1 mL of tetrahydrofuran were sequentially and slowly added dropwise, then the temperature was raised to room temperature, and the mixture was stirred under an argon atmosphere for 3 hours. The reaction solution was stirred again at −78° C. for 10 minutes, then Compound 3 (189 mg, 0.341 mmol) dissolved in 1 mL of tetrahydrofuran and triethylamine (94 μL, 0.684 mmol) were sequentially and slowly added dropwise, then the temperature was raised to room temperature, and the mixture was stirred overnight under an argon atmosphere. After the reaction was stopped by adding a saturated aqueous ammonium chloride solution, an aqueous layer was extracted using dichloromethane and ethyl acetate, the combined organic layers were dried using sodium sulfate, and the solvent was removed under reduced pressure. The residue was partially purified by silica gel column chromatography (ethyl acetate→ethyl acetate/methanol=97/3). After collecting a fraction containing the target compound, the solvent was removed by removal under reduced pressure, the residue was dissolved in 2 mL of acetonitrile, 8 mL of trifluoroacetic acid was added, and the mixture was stirred at room temperature for 1 hour. The residue obtained by removing the solvent under reduced pressure was purified by HPLC (eluent A ($H_2O$ 0.1% TFA) and eluent B ($CH_3CN$ 80%, $H_2O$ 20%, 0.1% TFA) (A/B=80/20 to 0/100 in 30 min)) to obtain Compound C (15 mg, 14%).

$^1$H NMR (400 MHz, $CD_3OD$): δ 1.15 (d, J=6.9 Hz, 2H), 1.24-1.38 (m, 10H), 1.51-1.78 (m, 3H), 1.78-1.98 (m, 1H), 2.40-2.56 (m, 3H), 3.06-3.24 (m, 2H), 3.91-4.11 (m, 1H), 4.25 (q, J=4.4 Hz, 0.37H), 4.39 (q, J=4.6 Hz, 0.63H), 6.30 (d, J=1.4 Hz, 1H), 7.12-7.22 (m, 0.37H), 7.22-7.29 (m, 1.63H), 7.76 (d, J=8.7 Hz, 0.37H), 7.80 (d, J=8.2 Hz, 0.63H) (diastereomer mixture, dr=63:37 judged from $^1$H NMR)

$^{13}$C NMR (100 MHz, DMSO-d6): δ 18.7, 21.6 (d, J=5.8 Hz), 22.0 (d, J=2.9 Hz), 24.7, 24.8, 25.5, 25.6, 28.7, 32.8 (d, J=132.2 Hz), 32.9 (d, J=132.2 Hz), 40.8, 50.3, 50.5, 51.9, 52.0, 108.8 (d, J=4.8 Hz), 109.3 (d, J=3.7 Hz), 113.4, 113.5, 116.5, 116.6, 117.7 (d, J=3.8 Hz), 118.3 (d, J=3.8 Hz), 126.8 (containing 2 peaks), 153.6, 153.7, 154.0, 154.1, 154.2, 154.3, 154.4, 157.3, 160.3, 160.4, 173.6, 173.7, 174.0 (d, J=1.6 Hz), 174.1 (d, J=4.8 Hz), $^{31}$P NMR (162 MHz, DMSO-d6): δ 39.5, 40.3

HRMS (ESI$^+$): calcd for [M+H]$^+$, 524.22741; found, 524.22696 (−0.45 mmu)

The UPLC (eluent; A/B=95/5 to 5/95 in 4 min) chromatogram after purification is shown. Absorbance at 310 nm was detected. Eluent A ($H_2O$ containing 0.1% formic acid) and eluent B (80% acetonitrile and 20% $H_2O$ containing 0.1% formic acid) were used for UPLC analysis.

Example 2

An enzyme assay using the synthesized Compound C and CPB was performed. As a result, while Compound C served as a substrate for CPB and showed the increase in fluorescence, as compared with Compound B, no increase in fluorescence was observed in the absence of enzyme, and it became clear that Compound C was stable at pH 7.4, which was a physiological condition (FIG. 4).

FIG. 4(a) illustrates a reaction scheme of Compound C and CPB. In FIG. 4(b), 10 μM Compound C in PBS (-) was incubated at 37° C. in the presence or absence of 5 ng CPB containing 0.1% DMSO as a co-solvent. Ex/Em=355/460 nm. n=4. FIG. 4(c) shows a comparison of stability of Compound A and Compound C. 10 μM Compound A or Compound C in PBS (-) was incubated at 37° C. in the absence of CPB. Ex/Em=355/460 nm. n=4.

From these results, in the present molecular design designed based on ProTide, a derivative having a t-Bu group as a substituent on a phosphorus atom was stable at pH 7.4, which was a physiological condition, and could cause the increase in fluorescence by reaction with carboxypeptidase. When a linker site in the present molecule is named tSoul (tBu Substituted phosphorus linker), 4MU-tSoul-AR, which is Compound C, can be said to be a blue probe that detects CPB activity.

On the other hand, in live imaging of carboxypeptidase in living cells and clinical specimens, it is desirable to increase the fluorescence wavelength from the viewpoint of cytotoxicity/autofluorescence. Thus, next, synthesis of a new probe HMRef-tSoul-AR having HMRef, which has green fluorescence as a fluorophore and has been reported to connect protecting/deprotecting reaction of a phenolic hydroxyl group to OFF/ON of fluorescence through a change in spiro cyclization equilibrium, was performed by the following scheme. HMRef was synthesized according to a literature (D. Asanuma, M. Sakabe, M. Kamiya, K. Yamamoto, J. Hiratake, M. Ogawa, N. Kosaka, P. L. Choyke, T. Nagano, H. Kobayashi, Y. Urano, Nat. Commun., 2015, 6, 6463.).

Scheme 3

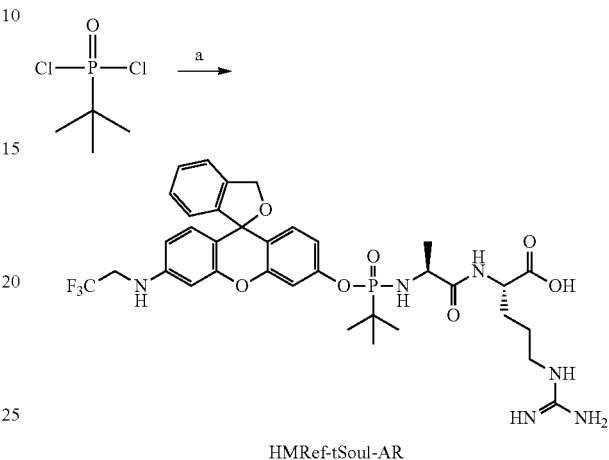

HMRef-tSoul-AR
(a) 1) HMRef, TEA, THF, 2) H-Ala-Arg (Pbf) ──OtBu, TEA, THF, 3) TFA, MeCN, 1.7% in 3 steps (diastereomer mixture).

Synthesis Example 31

Synthesis of HMRef-tSoul-AR

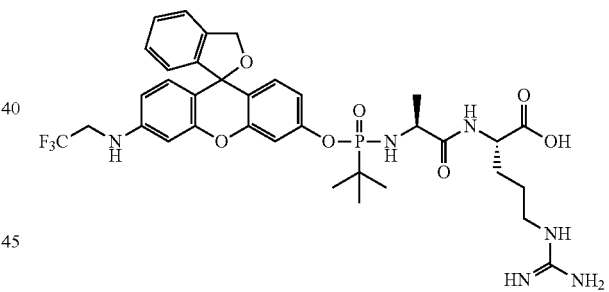

tert-Butylphosphonic acid dichloride (30 mg, 0.171 mmol) was dissolved in 1 mL of tetrahydrofuran, and the solution was stirred at −78° C. for 10 minutes under an argon atmosphere. HMRef (68 mg, 0.170 mmol) and triethylamine (47 μL, 0.342 mmol) dissolved in 1 mL of tetrahydrofuran were slowly added dropwise, then the temperature was raised to 35° C., and the mixture was stirred under an argon atmosphere for 4 hours. The reaction solution was stirred again at −78° C. for 10 minutes, then Compound 3 (188 mg, 0.334 mmol) dissolved in 1 mL of tetrahydrofuran and triethylamine (94 μL, 0.684 mmol) were sequentially and slowly added dropwise, then the temperature was raised to 60° C., and the mixture was stirred overnight under an argon atmosphere. After the reaction was stopped by adding a saturated aqueous ammonium chloride solution, an aqueous layer was extracted using ethyl acetate. The organic layer was dried with sodium sulfate, the solvent was removed under reduced pressure, and then the residue was partially purified by aminosilica gel column chromatography (dichloromethane→dichloromethane/methanol=93/7). After collecting a fraction containing the target compound, the solvent was removed by removal under reduced pressure, 2 mL of trifluoroacetic acid was added to the residue, and the mixture was stirred at room temperature for 2 hours. The solvent was removed by removal under reduced pressure, the residue was partially purified by HPLC (eluent A (H$_2$O 0.1% TFA) and eluent B (CH$_3$CN 80%, H$_2$O 20%, 0.1% TFA) (A/B=80/20 to 0/100 in 30 min)), and after collecting a fraction containing the target compound, the solvent was removed by removal under reduced pressure. The residue was partially purified by HPLC (eluent C (H$_2$O containing 100 mM triethylammonium acetate) and eluent D (80% acetonitrile and 20% H$_2$O containing 100 mM triethylammonium acetate) (C/D=80/20 to 0/100 in 30 min)), and after collecting a fraction containing the target compound, the solvent was removed by removal under reduced pressure. The residue was purified by HPLC (eluent E (H$_2$O) and eluent F (80% acetonitrile and 20% H$_2$O) (E/F=80/20 to 0/100 in 30 min)) to obtain a target compound HMRef-tSoul-AR (2.2 mg, 1.7%).

$^1$H NMR (400 MHz, CD$_3$OD): δ 1.07 (dd, J=7.3, 9.1 Hz, 1H), 1.19-1.33 (m, 11H), 1.33-1.87 (m, 4H), 2.79-2.95 (m, 1.3H), 3.08-3.18 (m, 0.7H), 3.82 (q, J=9.1 Hz, 2H), 3.88-3.99 (m, 1H), 4.07-4.22 (m, 1H), 5.21-5.29 (m, 2H), 6.44 (dd, J=2.3, 8.7 Hz, 1H), 6.48-6.55 (m, 1H), 6.66-6.73 (m, 1H), 6.78 (t, J=7.5 Hz, 1H), 6.84-6.94 (m, 2H), 7.05-7.13 (m, 1H), 7.21-7.31 (m, 1H), 7.33-7.44 (m, 2H) (diastereomer mixture)

HRMS (ESI$^+$): calcd for [M]$^+$, 747.28829; found, 747.28597 (−2.33 mmu)

The UPLC (eluent; C/D=95/5 to 5/95 in 4 min) chromatogram after purification is shown. Absorbance at 254 nm was detected. Eluent C (H$_2$O containing 10 mM ammonium formate) and eluent D (80% acetonitrile and 20% H$_2$O containing 10 mM ammonium formate) were used for UPLC analysis.

Example 3

Next, reactivity with CPB and the stability in a buffer solution having a pH of 7.4 were examined. As a result, it became clear that while HMRef-tSoul-AR caused a fluorescence increase of 3320 times by reaction with CPB, HMRef-tSoul-AR was stable for at least about 1 hour in the absence of enzyme. The results are illustrated in FIG. 5.

FIG. 5(a) illustrates a reaction scheme of HMRef-tSoul-AR and CPB. FIG. 5(b) illustrates the fluorescence increase of 1 μM HMRef-tSoul-AR in PBS (-) incubated with 30 μg CPB containing 0.1% DMSO as a co-solvent. Incubation was performed at 25° C. The excitation wavelength was 498 nm. FIG. 5(c) illustrates an absorption change of 1 μM HMRef-tSoul-AR in PBS (-) at 25° C. for 50 minutes.

In addition, an enzyme reaction rate parameter was calculated. Incidentally, although the reaction with CPB has been performed in the studies so far, it became clear that HMRef-tSoul-AR served as a substrate of carboxypeptidase M (CPM) preferred basic amino acid as a substrate similarly to CPB, and therefore, parameters were calculated for both enzymes. Since a background signal was sufficiently suppressed in the present probe, it was determined that an initial rate could be calculated by a fluorescence method even if a high-concentration probe was used, and the measurement was performed.

TABLE 1

Comparison of enzyme reaction rate parameter of probe
Table 4-3-1. Comparison of apparent kinetic parameters of the probes.

| | Enzyme | $K_m$ [M] | $V_{max}$ [M/s] | $k_{cat}$ [s$^{-1}$] | $k_{cat}/K_m$ [M$^{-1}$ s$^{-1}$] |
|---|---|---|---|---|---|
| HMRef-tSoul-AR | CPB | 5.0 × 10$^{-5}$ | 1.2 × 10$^{-8}$ | 1.7 | 3.4 × 10$^4$ |
| HMRef-tSoul-AR | CPM | 6.1 × 10$^{-5}$ | 4.0 × 10$^{-8}$ | 1.0 | 1.6 × 10$^4$ |

All experiments were performed at 37° C. in a total volume of 20 μL of phosphate buffered saline (pH 7.4) containing DMSO as a co-solvent. 5 ng of CPB or CPM was added. An enzyme reaction initial rate was calculated from a fluorescence change at 535 nm using a plate reader (n=3). The excitation wavelength was 485 nm.

When the reactivity with CPB was compared with diClHMRBC-CONH-Arg, which was a first generation probe, a value of $k_{cat}/K_m$ was increased by about one order in HMRef-tSoul-AR, and an increase in reactivity with enzyme was observed. From these results, it was determined that improvement of sensitivity of the probe could be achieved by the reactivity with enzyme and improvement in S/N, and live imaging of the carboxypeptidase activity in living cells, which could not be achieved by diClHMRBC-CONH-Arg, was performed.

Example 4

Live Imaging of Carboxypeptidase Activity in Live Cells

Live imaging of the carboxypeptidase activity in living cells was performed using HMRef-tSoul-AR synthesized above. Specifically, it was examined whether or not the increase in fluorescence was observed by adding a probe to MDCK cells expressing CPM in which it became clear that HMRef-tSoul-AR was used as a substrate. Since it has been reported that CPM is expressed as an active form on a cell membrane unlike CPB, addition of trypsin or the like is unnecessary.

As a result, it became clear that while an increase in fluorescence over time from the MDCK cells was observed, the increase in fluorescence was completely suppressed by the addition of MGTA as an inhibitor (FIG. 6).

Here, FIGS. 6(a) and 6(b) illustrate fluorescence images of the MDCK cells containing 10 μM HMRef-tSoul-AR in HBSS in the presence (a) or absence (b) of 10 μM MGTA. Ex/Em=488/500-550 nm laser output 5%, PMT 600 V. 10 μM Hoechst 33342 was co-incubated for focal plane correction. For imaging of a Hoechst signal, Ex/Em=405/430-460 nm. Laser output 3%, PMT 1000 V, SP8.

After an external liquid after incubation of 20 μM of HMRef-tSoul-AR for 20 hours was recovered and analyzed by UPLC, it was confirmed that HMRef was certainly generated (FIG. 7).

Here, FIG. 7 illustrates results of UPLC analysis of a medium of the MDCK cells incubated with 20 μM HMRef-tSoul-AR in the presence or absence of 10 μM MGTA. The MDCK cells were incubated with 20 μM HMRef-tSoul-AR in HBSS at 37° C. for 20 hours in the presence or absence of 10 μM MGTA. Elution was performed with a linear gradient of C/D=95/5 to 5/95 in 4 minutes and detected at 254 nm. These results are the world's first examples of a success in live imaging of CPM activity in living cells.

Example 5

Development of PSMA Activity Detection Fluorescent Probe

Using tSoul that has heretofore been developed, a prostate specific membrane antigen (PSMA) activity detection fluorescent probe, which has been established as a biomarker for prostate cancer, has been developed. PSMA has been reported to have an activity of cleaving C-terminal glutamic acid. Thus, 4-MU having blue fluorescence as a fluorophore, and 4MU-tSoul-AE having an alanine residue as T, a tBu group as $R^1$, and a glutamic acid residue as S in the general formula (I) were synthesized.

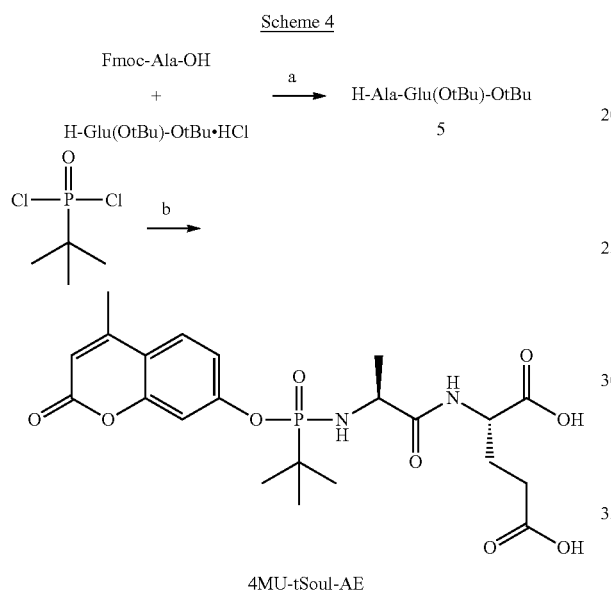

(a) 1) HATU, DIEA, DMF, 2) Piperidine, DMF, y. 85% in 2 steps. (b) 1) 4-MU, TEA, THF, 2) H-Ala-Glu(OtBu)-OtBu, TEA, THF, 2) TFA, MeCN, y. 14% in 3 steps, diastereomer mixture.

Synthesis of Compound 5

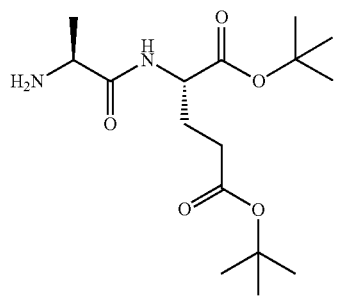 [SMILES: C[C@H](N)C(=O)N[C@@H](CCC(=O)OC(C)(C)C)C(=O)OC(C)(C)C]

Fmoc-Ala-OH (994 mg, 3.00 mmol), H-Glu(OtBu)-OtBu hydrochloride (886 mg, 3.00 mmol), and N, N-diisopropylethylamine (1548 µL, 9.29 mmol) were dissolved in 5 mL of N, N-dimethylformamide, and HATU (1254 mg, 3.30 mmol) was added and stirred at room temperature for 3 hours. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was partially purified by silica gel column chromatography (ethyl acetate/hexane=1/1), and after collecting a fraction containing the target compound, the solvent was removed by removal under reduced pressure. The residue was dissolved in 8 mL of N, N-dimethylformamide, 2 mL of piperidine was added thereto, and the mixture was stirred at room temperature for 90 minutes. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was purified by aminosilica gel column chromatography (dichloromethane→dichloromethane/methanol=97/3) to obtain Compound 5 (841 mg, 85%).

$^1$H NMR (400 MHz, CD$_3$OD): δ 1.28 (d, J=6.9 Hz, 3H), 1.45 (s, 9H), 1.47 (s, 9H), 1.76-1.98 (m, 1H), 1.99-2.20 (m, 1H), 2.32 (t, J=7.5 Hz, 2H), 3.44 (q, J=6.9 Hz, 1H), 4.31 (dd, J=5.3, 8.9 Hz, 1H), 13C NMR (100 MHz, CD$_3$OD): δ 20.3, 26.7, 26.9, 27.0, 31.2, 49.9, 52.2, 80.5, 81.7, 171.1, 172.3, 177.2

HRMS (ESI$^+$): calcd for [M+H]$^+$, 331.22330; found, 331.22158 (−1.72 mmu)

Synthesis of 4MU-tSoul-AE

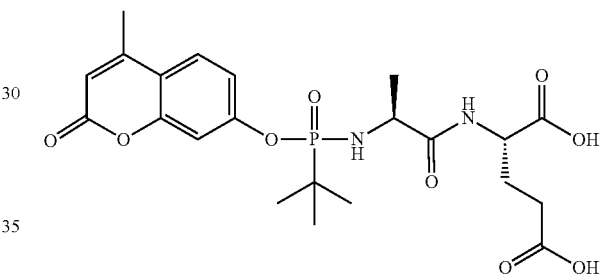

tert-Butylphosphonic acid dichloride (30 mg, 0.171 mmol) was dissolved in 2 mL of tetrahydrofuran, and the solution was stirred at −78° C. for 10 minutes under an argon atmosphere. 4-Methylumbelliferone (30 mg, 0.170 mmol) and triethylamine (48 µL, 0.349 mmol) dissolved in 1 mL of tetrahydrofuran were sequentially and slowly added dropwise, then the temperature was raised to room temperature, and the mixture was stirred under an argon atmosphere for 1 hour. The reaction solution was stirred again at −78° C. for 10 minutes, then Compound 5 (113 mg, 0.342 mmol) dissolved in 1 mL of tetrahydrofuran and triethylamine (96 µL, 0.698 mmol) were sequentially and slowly added dropwise, then the temperature was raised to room temperature, and the mixture was stirred overnight under an argon atmosphere. The temperature was raised to 60° C., and the mixture was further stirred for 3 hours. Then, after the reaction was stopped by adding a saturated saline solution, an aqueous layer was extracted using ethyl acetate, the combined organic layers were dried using sodium sulfate, and the solvent was removed under reduced pressure. The residue was partially purified by silica gel column chromatography (ethyl acetate/hexane=65/35→90/10). After collecting a fraction containing the target compound, the solvent was removed by removal under reduced pressure, the residue was dissolved in 2 mL of acetonitrile, 4 mL of trifluoroacetic acid was added, and the mixture was stirred at room temperature for 1 hour. The residue obtained by removing the solvent under reduced pressure was purified by HPLC (eluent A (H$_2$O 0.1% TFA) and eluent B (CH$_3$CN 80%, H₂O 20%, 0.1% TFA) (A/B=80/20 to 0/100 in 30 min)) to obtain Compound C (12 mg, 14%).

¹H NMR (400 MHz, CD₃OD): δ 1.04-1.40 (m, 12H), 1.60-1.79 (m, 0.48H), 1.79-2.05 (m, 1H), 2.06-2.25 (m, 1.52H), 2.30-2.37 (m, 1H), 2.40-2.53 (m, 3H), 3.87-4.08 (m, 1H), 4.22 (q, J=4.6 Hz, 0.48H), 4.38 (q, J=4.7 Hz, 0.52H), 6.25 (d, J=1.4 Hz, 0.48H), 6.27 (d, J=1.4 Hz, 0.52H), 7.12-7.31 (m, 2H), 7.66-7.85 (m, 1H) (diastereomer mixture, dr=13:12 judged from ¹H NMR)

¹³C NMR (100 MHz, CD₃OD): δ 17.3, 17.4, 19.9 (d, J=6.8 Hz), 20.5 (d, J=3.8 Hz), 23.3 (d, J=6.7 Hz), 26.5, 29.6, 32.4 (d, J=132.3 Hz), 32.5 (d, J=132.2 Hz), 50.4, 51.5 (containing 2 peaks), 108.9 (d, J=4.8 Hz), 109.0 (d, J=4.8 Hz), 113.0, 113.1, 116.9, 117.0, 117.4 (d, J=3.8 Hz), 117.6 (d, J=4.8 Hz), 126.1, 126.2, 153.5 (d, J=3.7 Hz), 153.6 (d, J=3.8 Hz), 153.7, 154.2 (containing 2 peaks), 161.3, 161.4, 172.9, 173.1, 174.5, 174.6 (containing 2 peaks), 174.7, 174.8

³¹P NMR (162 MHz, CD₃OD): δ 41.1, 41.6

HRMS (ESI⁺): calcd for [M+H]⁺, 497.16889; found, 467.16732 (−1.57 mmu)

The UPLC (eluent; A/B=95/5 to 5/95 in 4 min) chromatogram after purification is shown. Absorbance at 310 nm was detected. Eluent A (H₂O containing 0.1% formic acid) and eluent B (80% acetonitrile and 20% H2O containing 0.1% formic acid) were used for UPLC analysis.

An enzyme assay was performed using the synthesized 4MU-tSoul-AE and PSMA. As a result, contrary to expectations, the increase in fluorescence was not observed, and it became clear that 4MU-tSoul-AE was not recognized as a substrate (FIG. 8).

Here, 10 μM 4MU-tSoul-AE in TBS buffer was incubated at 37° C. with 22 ng PSMA in the presence or absence of 10 μM inhibitor (2-PMPA) containing 0.1% DMSO as a co-solvent. Ex/Em=355/460 nm. n=3.

Example 6

The probe was improved based on this result. It is suggested that not only C-terminal glutamic acid but also an adjacent amino acid residue are important for enzyme recognition of PSMA. Thus, a derivative in which T in the general formula (I) was changed to a different amino acid was synthesized. Considering that a PSMA enzymatic pocket was relatively small, 4-MU having blue fluorescence as a fluorophore with a small molecular size, and 4MU-tSoul-GE having a glycine residue as T, a tBu group as R¹, and a glutamic acid residue as S in the general formula (I) were synthesized.

Scheme 5

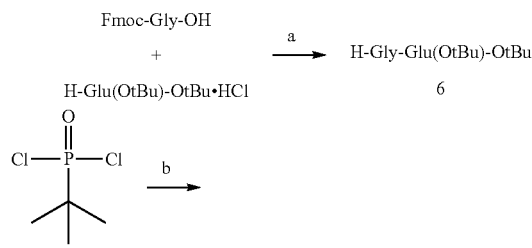

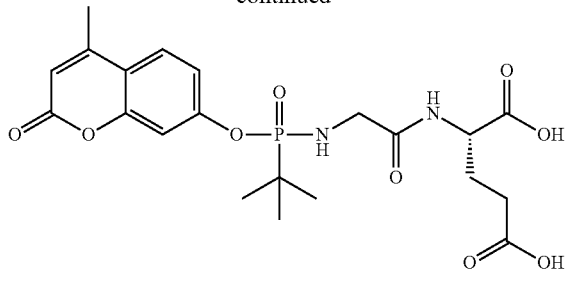

4MU-tSoul-GE (a) 1) HATU, DIEA, DMF, 2) Piperidine, DMF, y. 61% in 2 steps. (b) 1) 4-MU, TEA, THF, 2) H-Ala-Glu(OtBu)-OtBu, TEA, THF, 2) TFA, MeCN, y. 14% in 3 steps, diastereomer mixture.

Synthesis of Compound 6

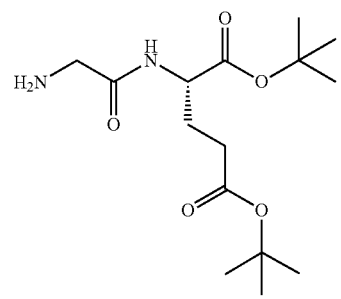 [SMILES: CC(C)(C)OC(=O)CC[C@H](NC(=O)CN)C(=O)OC(C)(C)C]

Fmoc-Gly-OH (594 mg, 2.00 mmol), H-Glu (OtBu)-OtBu hydrochloride (591 mg, 2.00 mmol), and N, N-diisopropylethylamine (1032 μL, 6.00 mmol) were dissolved in 10 mL of N, N-dimethylformamide, and HATU (1032 mg, 2.20 mmol) was added and stirred at room temperature for 90 minutes. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was partially purified by silica gel column chromatography (ethyl acetate/hexane=3/7→1/1), and after collecting a fraction containing the target compound, the solvent was removed by removal under reduced pressure. The residue was dissolved in 8 mL of N, N-dimethylformamide, 2 mL of piperidine was added thereto, and the mixture was stirred at room temperature for 2 hours. Ethyl acetate and a saturated aqueous ammonium chloride solution were added to the reaction solution, and an ethyl acetate layer was extracted by liquid separation operation. The extracted organic layer was dried over sodium sulfate, and then the solvent was removed by vacuum removal. The residue was purified by aminosilica gel column chromatography (ethyl acetate ethyl acetate/methanol=90 10) to obtain Compound 6 (385 mg, 61%).

¹H NMR (400 MHz, CDCl₃): δ 1.44 (s, 9H), 1.48 (s, 9H), 1.82-2.04 (m, 1H), 2.05-2.21 (m, 1H), 2.21-2.39 (m, 2H), 3.37 (s, 2H), 4.44-4.62 (m, 1H), 7.69 (d, J=8.2 Hz, 1H)

¹³C NMR (100 MHz, CD₃OD): δ 26.8, 26.9, 27.0, 31.1, 43.6, 52.2, 80.5, 81.8, 171.2, 172.2, 174.1

HRMS (ESI⁺): calcd for [M+Na]⁺, 339.18959; found, 339.18576 (−3.83 mmu)

Synthesis of 4MU-tSoul-GE

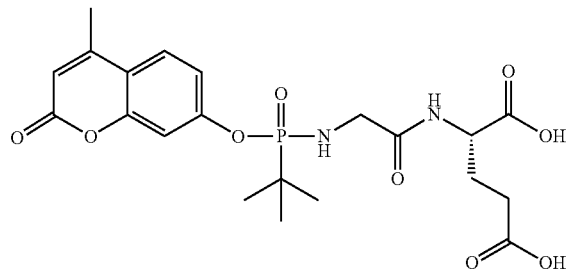 [SMILES: Cc1cc(=O)oc2cc(OP(=O)(NCC(=O)N[C@@H](CCC(=O)O)C(=O)O)C(C)(C)C)ccc12]

tert-Butylphosphonic acid dichloride (30 mg, 0.171 mmol) was dissolved in 2 mL of tetrahydrofuran, and the solution was stirred at −78° C. for 10 minutes under an argon atmosphere. 4-Methylumbelliferone (30 mg, 0.170 mmol) and triethylamine (48 µL, 0.349 mmol) dissolved in 1 mL of tetrahydrofuran were sequentially and slowly added dropwise, then the temperature was raised to 35° C., and the mixture was stirred under an argon atmosphere for 2 hours. The reaction solution was stirred again at −78° C. for 10 minutes, then Compound 6 (108 mg, 0.341 mmol) dissolved in 1 mL of tetrahydrofuran and triethylamine (96 µL, 0.698 mmol) were sequentially and slowly added dropwise, then the temperature was raised to 60° C., and the mixture was stirred overnight under an argon atmosphere. After the reaction was stopped by adding a saturated saline solution, an aqueous layer was extracted using ethyl acetate. The combined organic layers were washed with a saturated aqueous ammonium chloride solution and then dried using sodium sulfate, and the solvent was removed under reduced pressure. The residue was partially purified by aminosilica gel column chromatography (ethyl acetate/hexane=1/1→ethyl acetate). After collecting a fraction containing the target compound, the solvent was removed by removal under reduced pressure, the residue was dissolved in 2 mL of acetonitrile, 6 mL of trifluoroacetic acid was added, and the mixture was stirred at room temperature for 2 hours. The residue obtained by removing the solvent under reduced pressure was purified by HPLC (eluent A ($H_2O$ 0.1% TFA) and eluent B ($CH_3CN$ 80%, $H_2O$ 20%, 0.1% TFA) (A/B=80/20 to 0/100 in 30 min)) to obtain Compound C (18 mg, 22%).

$^1$H NMR (400 MHz, $CD_3OD$) δ 1.32 (d, J=17.4 Hz, 9H), 1.60-1.92 (m, 1H), 1.95-2.16 (m, 1H), 2.16-2.38 (m, 2H), 2.38-2.57 (m, 3H), 3.57-3.82 (m, 2H), 4.30-4.49 (m, 1H), 6.21-6.36 (m, 1H), 7.17-7.37 (m, 2H), 7.69-7.87 (m, 1H) (diastereomer mixture)

$^{13}$C NMR (100 MHz, $CD_3OD$): δ 17.3, 23.4, 26.7, 26.9, 29.5, 29.6, 32.8 (d, J=130.3 Hz), 43.9 (d, J=4.8 Hz), 51.2, 51.5, 108.8 (d, J=4.8 Hz), 109.9 (d, J=4.8 Hz), 113.1, 113.2, 117.0, 117.2, 117.4 (d, J=4.8 Hz), 117.5 (d, J=4.8 Hz), 126.3, 126.4, 153.3 (d, J=10.5 Hz), 153.5 (d, J=10.5 Hz), 154.3 (containing 2 peaks), 161.4 (containing 2 peaks), 171.3 (containing 2 peaks), 172.9 (containing 2 peaks), 174.7 (containing 2 peaks)

$^{31}$P NMR (162 MHz, $CD_3OD$): δ 42.5, 42.8

HRMS (ESI$^+$): calcd for [M+Na]$^+$, 505.13519; found, 505.13393 (−1.25 mmu)

The UPLC (eluent; A/B=95/5 to 5/95 in 4 min) chromatogram after purification is shown. Absorbance at 310 nm was detected. Eluent A ($H_2O$ containing 0.1% formic acid) and eluent B (80% acetonitrile and 20% $H_2O$ containing 0.1% formic acid) were used for UPLC analysis.

An enzyme assay was performed using the synthesized 4MU-tSoul-GE and PSMA. As a result, the increase in fluorescence was observed in the presence of PSMA, and the increase in fluorescence was suppressed by addition of 2-PMPA as an inhibitor. From this result, it became clear that 4MU-tSoul-GE functioned as a PSMA activity detection fluorescent probe. It can be said that this indicates strength of the present molecular design in which not only C-terminal amino acid to be cleaved by carboxypeptidase but also a structure of adjacent amino acid can be flexibly selected (FIG. 9).

Here, FIG. 9(a) illustrates a reaction scheme of 4MU-tSoul-GE and PSMA. In FIG. 9(b), 10 µM 4MU-tSoul-GE in TBS buffer was incubated at 37° C. with 22 ng PSMA in the presence or absence of 10 µM inhibitor (2-PMPA) containing 0.1% DMSO as a co-solvent. Ex/Em=355/460 nm. n=3.

Example 7

Breast Cancer Imaging Using HMRef-tSoul-AR

Examination of Examples 3 to 4 above revealed that HMRef-tSoul-AR reacted with CPB and CPM in vitro, and that the CPM activity of the MDCK cells could be live-imaged. Based on these results, whether or not cancer imaging could be performed by applying HMRef-tSoul-AR to a clinical specimen derived from a cancer patient was examined.

As summarized in Table 2, a plurality of carboxypeptidases that prefer basic amino acid as a substrate are present in vivo, and some of the carboxypeptidases have been reported to be associated with cancer. Although whether HMRef-tSoul-AR is a substrate for these is not currently known, it can be sufficiently expected that HMRef-tSoul-AR reacts with subtypes other than CPB and CPM. Thus, imaging for breast cancer in which the association of CPD, CPE (variant), and CPN among these subtypes has been reported has been attempted. Since these carboxypeptidases are present as activators like CPM, addition of trypsin or the like is unnecessary.

TABLE 2

| | Association with cancer |
|---|---|
| CPB (proCPB) | Pancreatic cancer |
| CPD | Prostate cancer, breast cancer |
| CPE | Several forms of cancer including breast cancer |
| CPM | Several forms of cancer |
| CPN | Breast cancer |
| CPU (proCPU) | Unknown |
| CPZ | Unknown |

Four specimens (IDC: invasive ductal carcinoma, 3 cases; DCIS: ductal carcinoma in situ, 1 case) derived from breast cancer patients were subjected to fluorescence imaging by applying HMRef-tSoul-AR to a tumor site and a normal site by the following procedure (FIG. 10).

HMRef-tSoul-AR was dissolved in PBS so as to have a final concentration of 50 µM (containing 1% DMSO), and applied to clinical specimens from breast cancer patients in the presence and absence of 100 µM MGTA. A fluorescence image was captured on Maestro in vivo imaging system (PerkinElmer, Inc., MA, USA), a 455 nm (435-480 nm) band pass filter was used as an excitation light filter, and a 490 nm long pass filter was used as a fluorescence filter.

When an increase was observed, in order to examine whether or not the increase was derived from basic carboxypeptidase activity, a group to which the inhibitor MGTA was added was also examined at the same time. MGTA is known to widely inhibit carboxypeptidase that prefers basic amino acid.

As a result, a remarkable increase in fluorescence was observed from a tumor tissue as compared with a normal tissue, and the increase in fluorescence was suppressed by the addition of MGTA. T/N calculated from fluorescence intensity after 60 minutes was 2.39 to 10.66, and strong fluorescence was certainly observed from the tumor site. Since the increase in fluorescence was suppressed in the presence of the inhibitor, it was considered that there was no problem in interpreting that most of the increase in fluorescence was due to the carboxypeptidase activity.

From the above results, it was shown that imaging of breast cancer could be performed by using the developed probe HMRef-tSoul-AR, and the increase in fluorescence was due to enhancement of the carboxypeptidase activity in a breast cancer tissue.

Although involvement of basic carboxypeptidase in breast cancer has heretofore been reported, these results are based on results of activity evaluation and immunostaining in a lysated sample, and it has been confirmed for the first time by the present invention that the activity is actually enhanced in a state where a form of tissue is maintained. It can be said that this is a finding obtained for the first time by performing live imaging with low invasiveness, and it can be said that this shows usefulness of the present probe.

What is claimed is:
1. A compound represented by the following general formula (I) or a salt thereof,

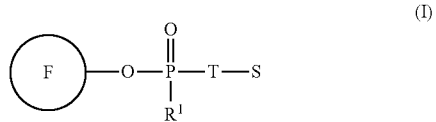

(I)

wherein $R^1$ represents an alkyl group having 1 to 6 carbon atoms or an alkoxy group having 1 to 6 carbon atoms;

T represents an amino acid residue or a residue of an amino acid derivative, wherein the amino acid residue is a residue of an amino acid selected from the group consisting of glycine, alanine, leucine, isoleucine, valine, lysine, cysteine, threonine, arginine, asparagine, aspartic acid, glutamine, glutamic acid, serine, histidine, phenylalanine, methionine, tryptophan, tyrosine, and proline, wherein the amino acid derivative is selected from the group consisting of N-methylleucine, 2,3-diaminopropanoic acid, 2,4-diaminobutyric acid, ornithine, and α-hydroxyleucine;

S represents a C-terminal amino acid residue; and

represents a fluorophore, and
the fluorophore is represented by the following formulas (3) to (6);

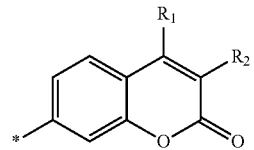

wherein, $R_1$ represents hydrogen or an alkyl group having 1 to 6 carbon atoms;

$R^2$ represents hydrogen, a carboxyl group, or an ester group of formula —COOR, wherein R represents an alkyl group having 1 to 6 carbon atoms;

* represents a bond to —O—P(=O)(—$R^1$)-T-S,

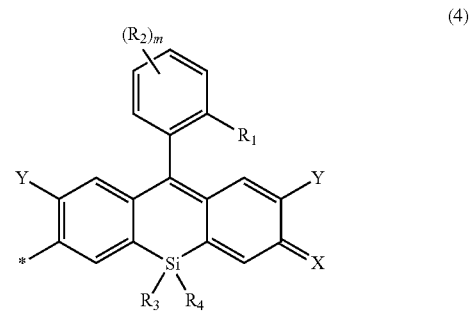

wherein, $R_1$ represents a hydrogen atom, an alkyl group having 1 to 6 carbon atoms, an alkoxyl group having 1 to 6 carbon atoms, or a carboxyl group;

$R_2$, when present, represents the same or different monovalent substituents present on the benzene ring, and said monovalent substituent is selected from an alkyl group having 1 to 6 carbon atoms, an alkoxyl group having 1 to 6 carbon atoms or a carboxyl group;

m is an integer of 0 to 4, and when m is 2 or more, each $R_2$ may be the same or different;

Y each independently represents a hydrogen atom, an alkyl group having 1 to 6 carbon atoms or a halogen atom;

$R_3$ and $R_4$ each independently represent an alkyl group or aryl group having 1 to 6 carbon atoms, when $R_3$ or $R_4$ represents an alkyl group, one or more of halogen atoms, carboxy groups, sulfonyl groups, hydroxy groups, amino groups, or alkoxy groups may be present on the alkyl group, when $R_3$ or $R_4$ represents an aryl group, the aryl group may be a monocyclic aromatic group or condensed aromatic group, and the aryl ring may include one or more ring-structured heteroatoms;

X is an oxygen atom of NR, wherein R represents a hydrogen atom or a substituted or unsubstituted alkyl group having 1 to 6 carbon atoms;

* represents a bond to —O—P(=O)(—R$^1$)-T-S,

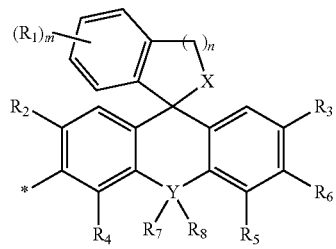

(5)

wherein,

R$_1$, when present, represents the same or different monovalent substituents present on the benzene ring, and said monovalent substituent is selected from an alkyl group having 1 to 6 carbon atoms, an alkoxyl group having 1 to 6 carbon atoms or a carboxyl group;

m is an integer of 0 to 4, and when m is 2 or more, each R$_1$ may be the same or different;

R$_2$ and R$_3$ are each independently a hydrogen atom, an alkyl group having 1 to 6 carbon atoms or a halogen atom, when R$_2$ or R$_3$ represents an alkyl group, one or more of halogen atoms, carboxy groups, sulfonyl groups, hydroxy groups, amino groups, or alkoxy groups may be present on the alkyl group;

R$_4$ and R$_5$ are each independently a hydrogen atom, an alkyl group having 1 to 6 carbon atoms, or a halogen atom;

R$_6$ is selected from NH$_2$, NHR, NRR', OH, or OR", wherein R and R' each independently represent an alkyl group having 1 to 5 carbon atoms or a fluoroalkyl group having 1 to 5 carbon atoms, R" represents an alkyl group having 1 to 5 carbon atoms;

Y represents an oxygen atom, a silicon atom, a carbon atom, or a phosphorus atom;

when Y is a phosphorus atom, one of R$_7$ and R$_8$ is =O;

when Y is an oxygen atom, R$_7$ and R$_8$ are not present;

R$_7$ and R$_8$, when present, each independently represent an alkyl group or aryl group having 1 to 6 carbon atoms, when R$_7$ or R$_8$ represents an alkyl group, one or more substituents selected from halogen atoms, carboxy groups, sulfonyl groups, hydroxy groups, amino groups, or alkoxy groups may be present on the alkyl group, when R$_7$ or R$_8$ represents an aryl group, the aryl group may be a monocyclic aromatic group or condensed aromatic group, the aryl ring may include one or more ring-structured heteroatoms, and one or more substituents selected from a halogen atom, carboxy group, sulfonyl group, hydroxy group, amino group, or alkoxy group may be present on the aryl ring;

X represents an oxygen atom or NRa, wherein Ra represents a hydrogen atom or an alkyl group having 1 to 5 carbon atoms;

n is an integer of 1 to 3;

* represents a bond to —O—P(=O)(—R$^1$)-T-S,

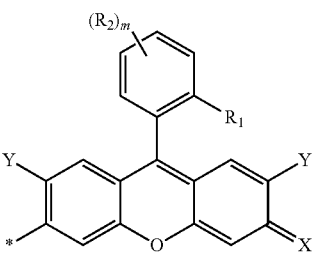

(6)

wherein,

R$_1$ represents a hydrogen atom, an alkyl group having 1 to 6 carbon atoms, an alkoxyl group having 1 to 6 carbon atoms or a carboxyl group;

R$_2$, when present, represents the same or different monovalent substituents present on the benzene ring, and said monovalent substituent is selected from an alkyl group having 1 to 6 carbon atoms, an alkoxyl group having 1 to 6 carbon atoms or a carboxyl group;

m is an integer of 0 to 4, and when m is 2 or more, each R$_2$ may be the same or different;

Y each independently represents a hydrogen atom, an alkyl group having 1 to 6 carbon atoms or a halogen atom;

X is an oxygen atom or NR, wherein R represents a hydrogen atom or a substituted or unsubstituted alkyl group having 1 to 6 carbon atoms; and

* represents a bond to —O—P(=O)(—R$^1$)-T-S.

2. A carboxypeptidase activity-detecting fluorescent probe comprising the compound or salt thereof according to claim 1.

3. A carboxypeptidase detection kit comprising the fluorescent probe according to claim 2.

4. A method of detecting activity of a carboxypeptidase, comprising:
(a) introducing the compound or salt thereof according to claim 1 into a cell; and
(b) measuring a fluorescence emitted when the compound or salt thereof reacts with a carboxypeptidase in the cell.

5. The detection method according to claim 4, wherein the fluorescence response is visualized using a fluorescence imaging means.

* * * * *